US010751398B2

(12) United States Patent
Qiao et al.

(10) Patent No.: US 10,751,398 B2
(45) Date of Patent: Aug. 25, 2020

(54) INFLAMMASOME ACTIVATORS AND METHODS OF USE TO TREAT TUMORS

(71) Applicant: Loyola University of Chicago, Maywood, IL (US)

(72) Inventors: Liang Qiao, Woodridge, IL (US); Zhenyu Zhong, San Diego, CA (US); Yougang Zhai, Countryside, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 15/728,460

(22) Filed: Oct. 9, 2017

(65) Prior Publication Data

US 2018/0243390 A1 Aug. 30, 2018

Related U.S. Application Data

(60) Provisional application No. 62/405,279, filed on Oct. 7, 2016.

(51) Int. Cl.
*A61K 39/12* (2006.01)
*A61K 39/00* (2006.01)
*A61P 35/00* (2006.01)

(52) U.S. Cl.
CPC .......... *A61K 39/0011* (2013.01); *A61K 39/12* (2013.01); *A61P 35/00* (2018.01); *A61K 2039/5256* (2013.01); *A61K 2039/5258* (2013.01); *A61K 2039/585* (2013.01); *A61K 2039/828* (2018.08); *A61K 2039/836* (2018.08); *C12N 2710/20023* (2013.01); *C12N 2710/20034* (2013.01)

(58) Field of Classification Search
None
See application file for complete search history.

(56) References Cited

U.S. PATENT DOCUMENTS

| | | | | |
|---|---|---|---|---|
| 2005/0142115 A1* | 6/2005 | Qiao | ........................ | C12N 7/00 424/93.2 |
| 2008/0311137 A1* | 12/2008 | La Monica | ...... | C07K 14/70503 424/184.1 |
| 2010/0135902 A1* | 6/2010 | Roberts | .................. | A61K 35/76 424/1.17 |
| 2012/0225090 A1* | 9/2012 | Wu | ..................... | A61K 31/7088 424/186.1 |

FOREIGN PATENT DOCUMENTS

WO WO-2012155007 A1 * 11/2012 ........... A61K 39/092

OTHER PUBLICATIONS

Kochar et al., "Totally One-sided: Painless Unilateral Proptosis," The American Journal of Medicine, vol. 128, No. 4 (Year: 2015).*

* cited by examiner

*Primary Examiner* — M Franco G Salvoza
(74) *Attorney, Agent, or Firm* — Hartman Global IP Law; Gary M. Hartman; Domenica N. S. Hartman

(57) ABSTRACT

Compositions and treatments for inducing tumor regression by activating inflammasomes in tumor cells and tumor-associated cells. A tumor in a subject is treated by administering a composition to the subject that activates inflammasomes in cells of the tumor and thereby causes tumor cell pyroptosis and tumor regression.

13 Claims, 26 Drawing Sheets

Specification includes a Sequence Listing.

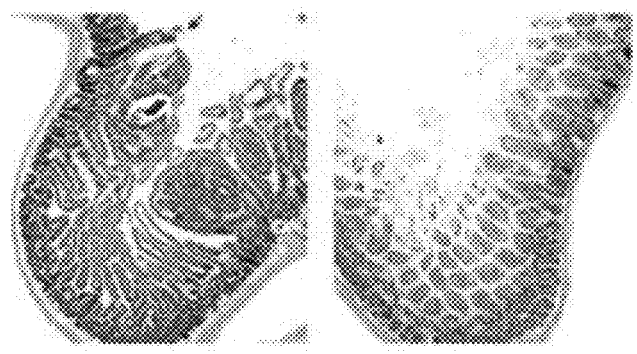
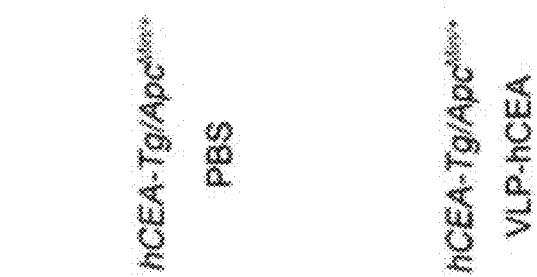
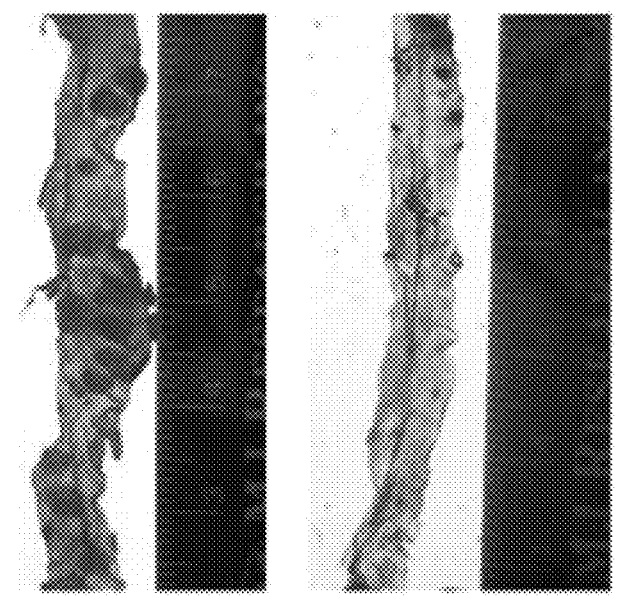
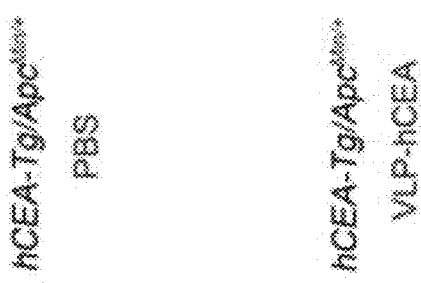
FIG. 1A
FIG. 1B

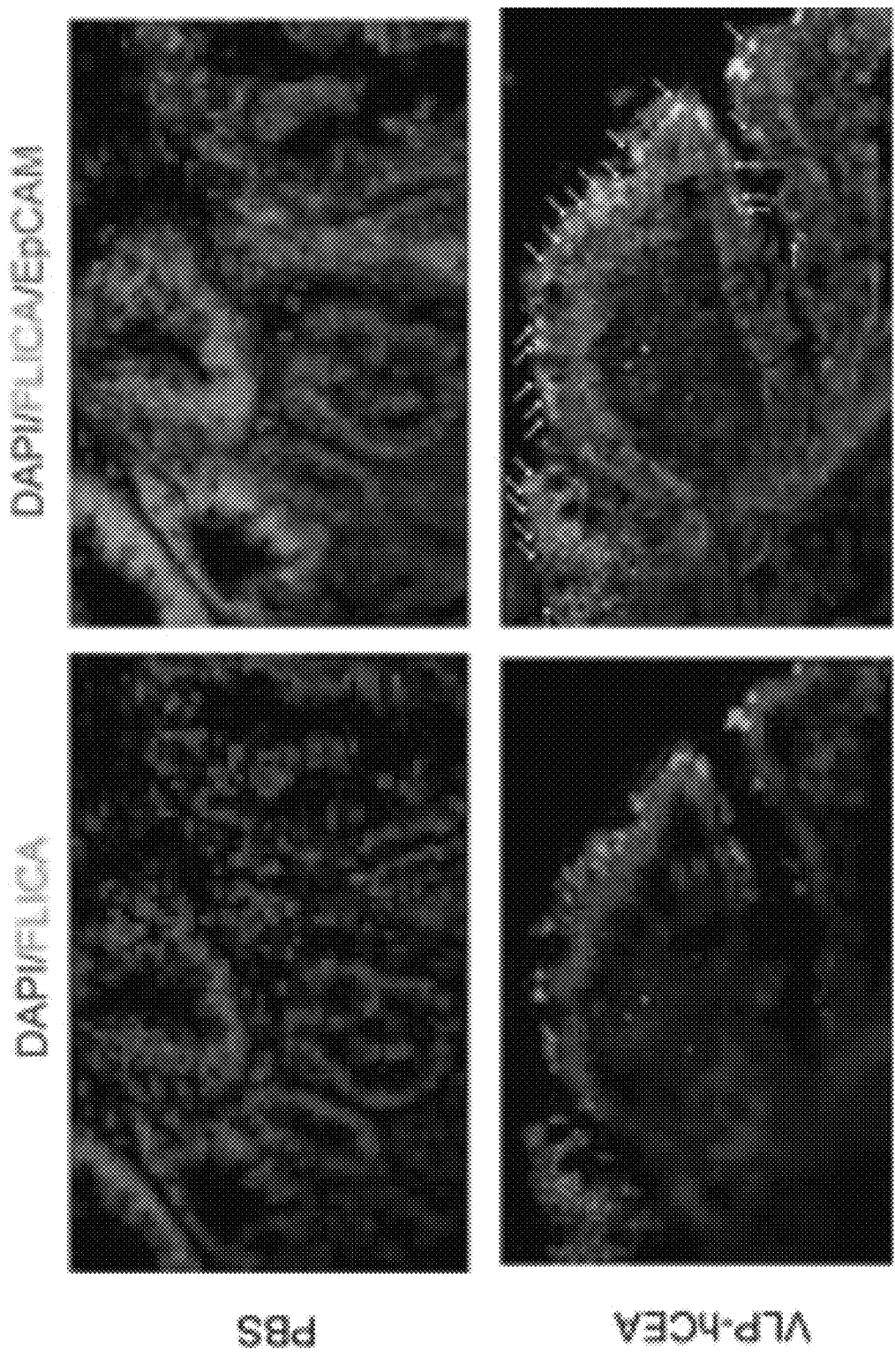

INFLAMMASOME ACTIVATORS AND METHODS OF USE TO TREAT TUMORS

CROSS REFERENCE TO RELATED APPLICATIONS

This application claims the benefit of U.S. Provisional Application No. 62/405,279, filed Oct. 7, 2016, the contents of which are incorporated herein by reference.

SEQUENCE LISTING

The instant application contains a Sequence Listing which has been submitted electronically in ASCII format and is hereby incorporated by reference in its entirety. Said ASCII copy, created on May 11, 2018, is named B7-5026_SL.TXT and is 9,148 bytes in size.

BACKGROUND OF THE INVENTION

The present invention generally relates to treatments for tumors, including but not limited to intestinal tumors. The invention particularly relates to the use of inflammasome activators, including but not limited to papilloma pseudoviruses and papilloma virus-like particles (VLP), to induce tumor regression in a patient.

As a component of gut mucosa, intestinal epithelial cells (IECs) absorb nutrients, provide a niche for commensal bacteria, and prevent invasion of harmful pathogens. However, when the biogenesis of IECs is dysregulated, which may occur as a result of an inherited genetic mutation, it can lead to the development of intestinal tumors. Conventional tumor vaccines aiming at inducing tumor-antigen specific immunity have shown limited efficacy in clinical trials, which may be due to an immunosuppressive microenvironment in the tumors.

Accordingly, it would be beneficial if a method were available that was capable of treating intestinal tumors by initiating an effective anti-tumor immune response.

BRIEF DESCRIPTION OF THE INVENTION

The present invention provides compositions and methods for treating subjects to induce gastro-intestinal tumor regression by activating inflammasomes in tumor cells and tumor-associated cells.

According to one aspect of the invention, a method is provided for treating a tumor in a subject that includes administering a composition to the subject, wherein the composition activates inflammasomes in cells of the tumor and thereby causes tumor cell pyroptosis and tumor regression.

According to another aspect of the invention, an inflammasome activator (as nonlimiting examples, a papilloma pseudovirus or papilloma virus-like particle) is provided that includes a plasmid that encodes a tumor-associated antigen, wherein the inflammasome activator activates inflammasomes in tumors upon being delivered to the tumors.

Technical effects of aspects of the invention described above preferably include the ability to cause activation of inflammasomes leading to tumor cell pyroptosis and tumor regression in tumors, as a nonlimiting example, an intestinal tumor.

Other aspects and advantages of this invention will be further appreciated from the following detailed description.

DETAILED DESCRIPTION OF THE INVENTION

Figure 1C:
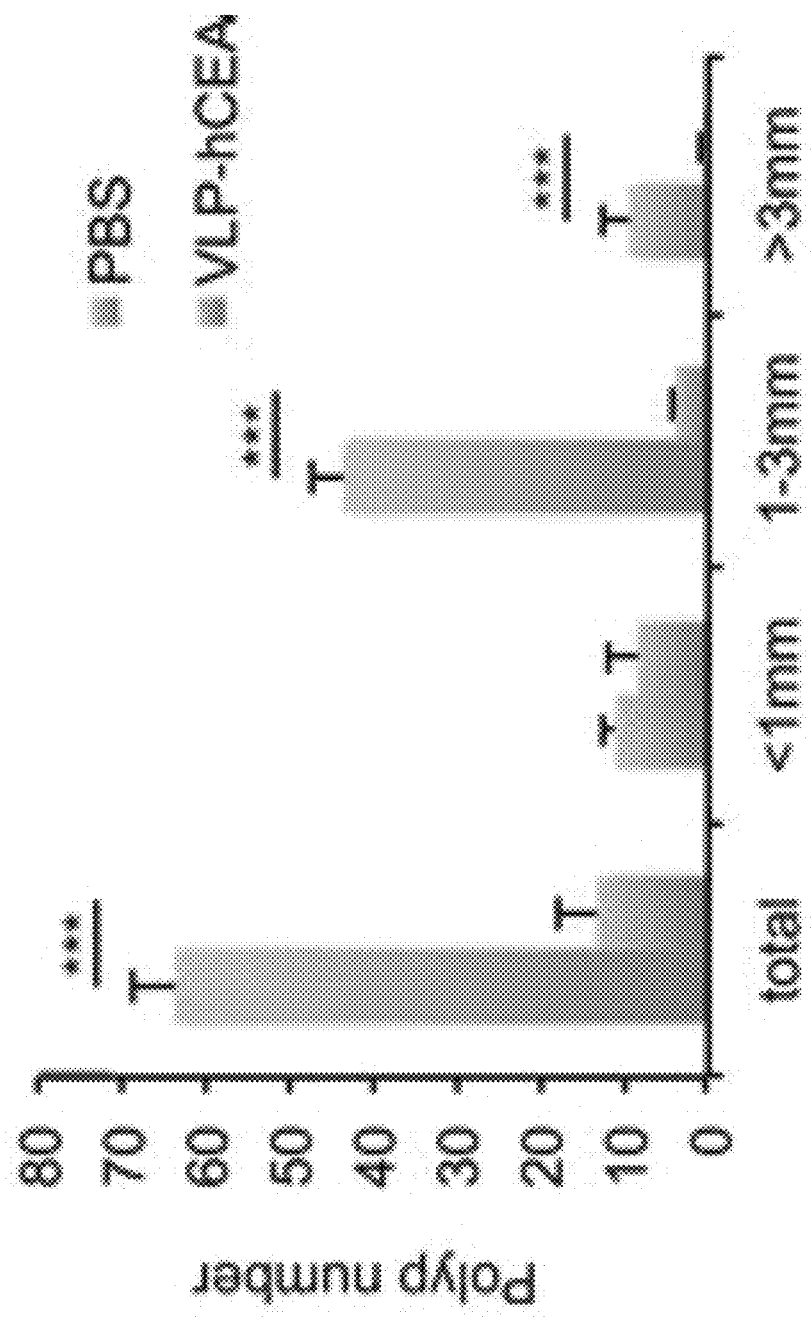
FIG. 1 includes images A through G representing data indicating that VLP-hCEA eradicated intestinal tumors and substantially extended the lifespan of hCEA-Tg/Apc$^{Min/+}$ mice. (A) Methylene blue staining of the small intestines from hCEA-Tg/Apc$^{Min/+}$ mice that were immunized with either PBS or VLP-hCEA pseudovirus (PsV). (B) Representative H and E staining of small intestines after PBS or VLP-hCEA oral immunization in hCEA-Tg/Apc$^{Min/+}$ mice. (C) The number of intestinal polyps of different sizes from hCEA-Tg/Apc$^{Min/+}$ mice (n=7 for both groups) that were immunized as in B. *, p<0.001. (D) Representative pictures of spleens from PBS or VLP-hCEA immunized hCEA-Tg/Apc$^{Min/+}$ mice. (E) The ratios of mouse spleen to whole body weight of hCEA-Tg/Apc$^{Min/+}$ mice (n-7 for both groups) that were immunized as described in B.*, p<0.001. (F) Survival of hCEA-Tg/Apc$^{Min/+}$ mice that were immunized with PBS (n=8) or VLP-hCEA (n=24). (G) Body weights of 20-week old hCEA-Tg/Apc$^{Min/+}$ mice that were immunized with either PBS (n=8) or VLP-hCEA (n=10).

The present invention provides compositions and methods of treating patients suitable for inducing intestinal tumor regression by activating inflammasomes in a subject, for example, a human cancer patient with advanced tumors. In particular, a papilloma pseudovirus (PsV) including a plasmid that encodes a tumor-associated antigen may be produced and administered to a subject to activate inflammasomes in mucosal tumors therein. Preferably, activation of the inflammasomes leads to tumor cell pyroptosis and tumor regression in an intestinal tumor. The papilloma pseudovirus may be produced by any methods known in the art. Exemplary methods suitable for producing the papilloma pseudovirus are disclosed in U.S. Pat. No. 6,878,541 to Qiao et al., the contents of which are incorporated herein by reference. The papilloma pseudovirus may be administered by any means known in the art, such as oral administration, and may be in any suitable dosages sufficient to cause tumor regression.

Mucosal IECs and immune cells express a number of innate immune sensors, such as Toll-like receptors (TLRs) and Nod-like receptors (NLRs), for pathogen recognition. Activation of these immune sensors induces production of messengers (i.e. chemokines/cytokines) that further recruit immune cells (e.g. phagocytes, dendritic cells, and adaptive immune cells) to join the battle against the invading pathogens. In epithelial cells-derived tumors (e.g. intestinal tumors), tumor cells and tumor-associated myeloid cells express TLRs/NLRs. The present invention is intended to cause expression of these receptors to initiate an immune response and thereby induce adaptive immunities against tumors, despite immunosuppressive mediators generally produced by tumor-associated myeloid cells in the gut that often blunt the beneficial immune responses elicited upon vaccination.

Nonlimiting embodiments of the invention will now be described in reference to experimental investigations leading up to the invention.

In one investigation leading to the present invention, experiments were designed to treat intestinal tumors using a papilloma pseudovirus (PsV) that encodes a tumor-associated antigen. Introduction of the tumor-specific antigen was intended to enable dissection of the roles of innate and tumor-antigen-specific adaptive immunities in tumor regression, if any. In the investigation, a tumor-associated antigen (human carcinoembryonic antigen, hCEA) was introduced into intestinal tumors in $Apc^{Min/+}$ mice by crossing the $Apc^{Min/+}$ mice with human CEA-transgenic (hCEA-Tg) mice. The progeny hCEA-Tg/$Apc^{Min/+}$ mice had roughly similar kinetics of tumorigenesis as their parental $Apc^{Min/+}$ mice. Importantly, these mice had hCEA expression along the intestinal epithelia, with specific elevation in intestinal tumor cells, which mimics patients with familial adenomatous polyposis. A PsV was produced which was comprised of bovine papilloma virus-like particles (made of viral L1 protein) with a hCEA-expressing DNA plasmid (pUMVC3-hCEA) packaged inside. This pseudovirus (referred to as VLP-hCEA) was able to induce hCEA expression in systemic and intestinal antigen-presenting cells (data not shown).

Figures 1D, 1E:
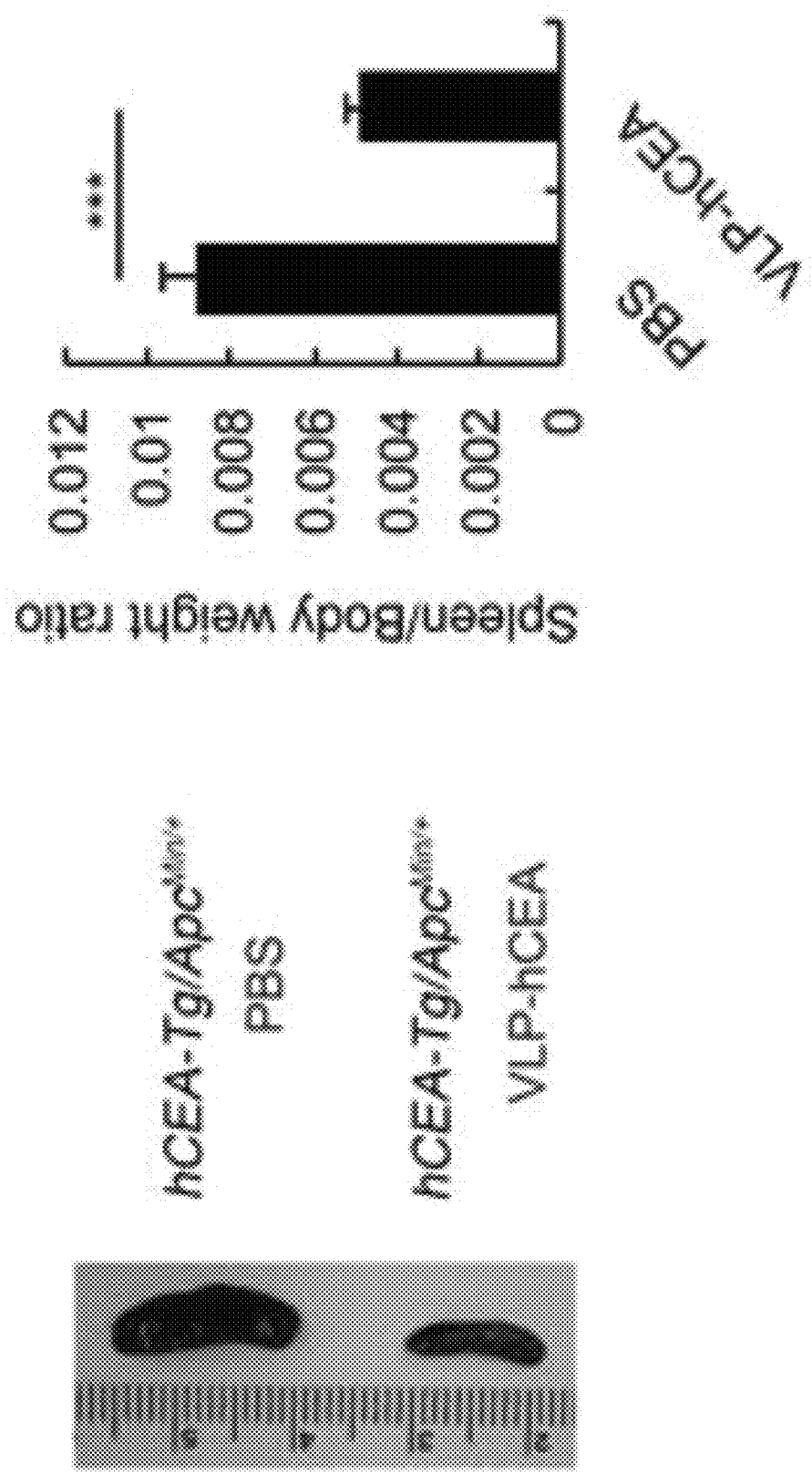
Figure 1G:
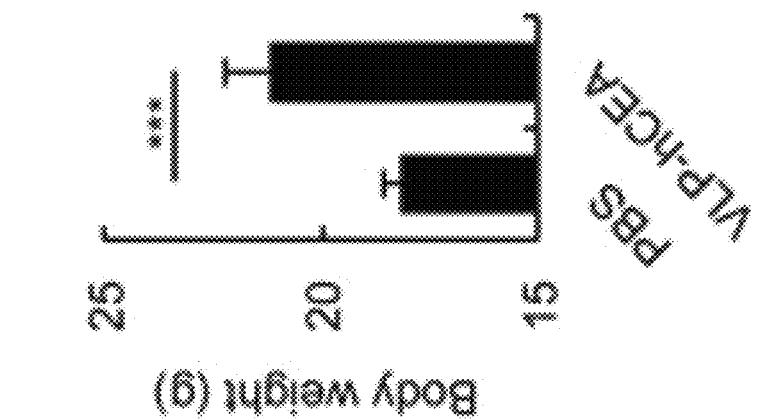
Figure 1F:
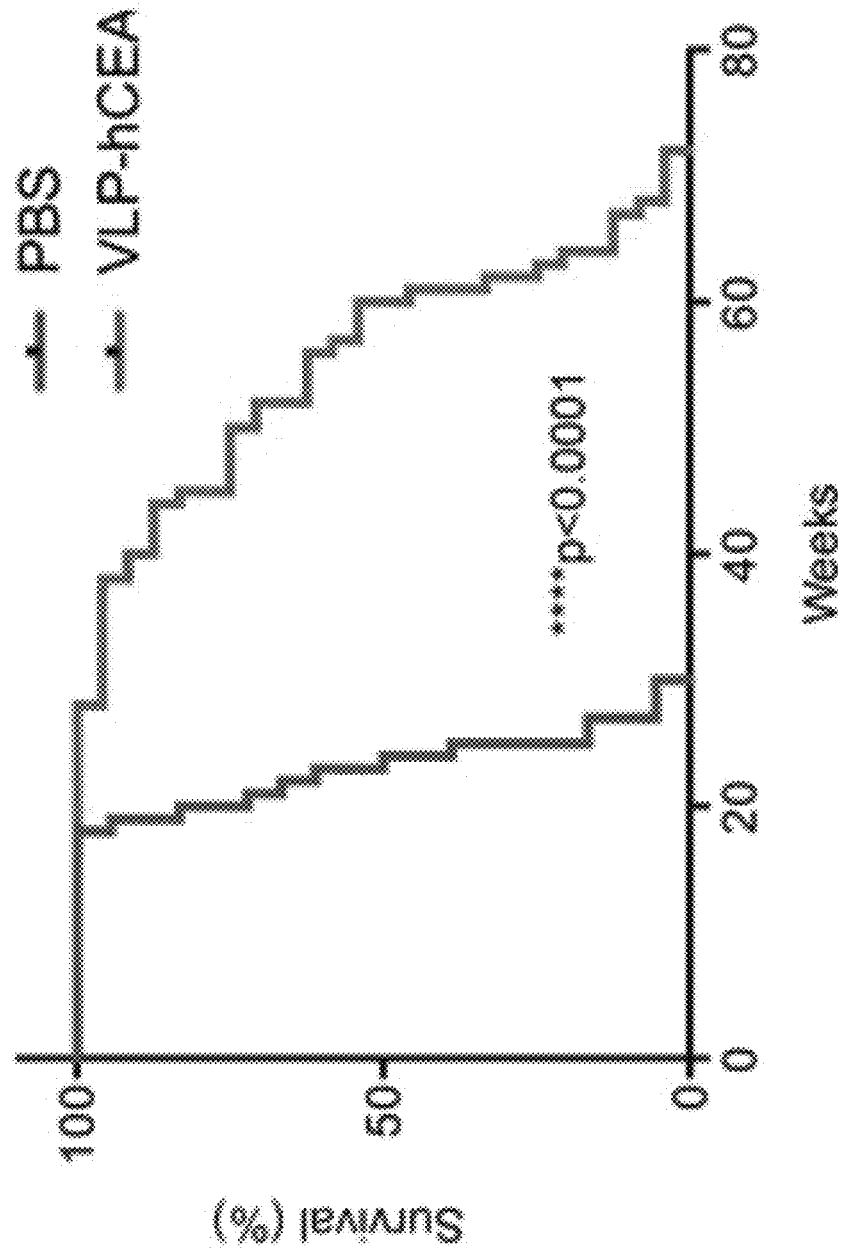
Figure 6:
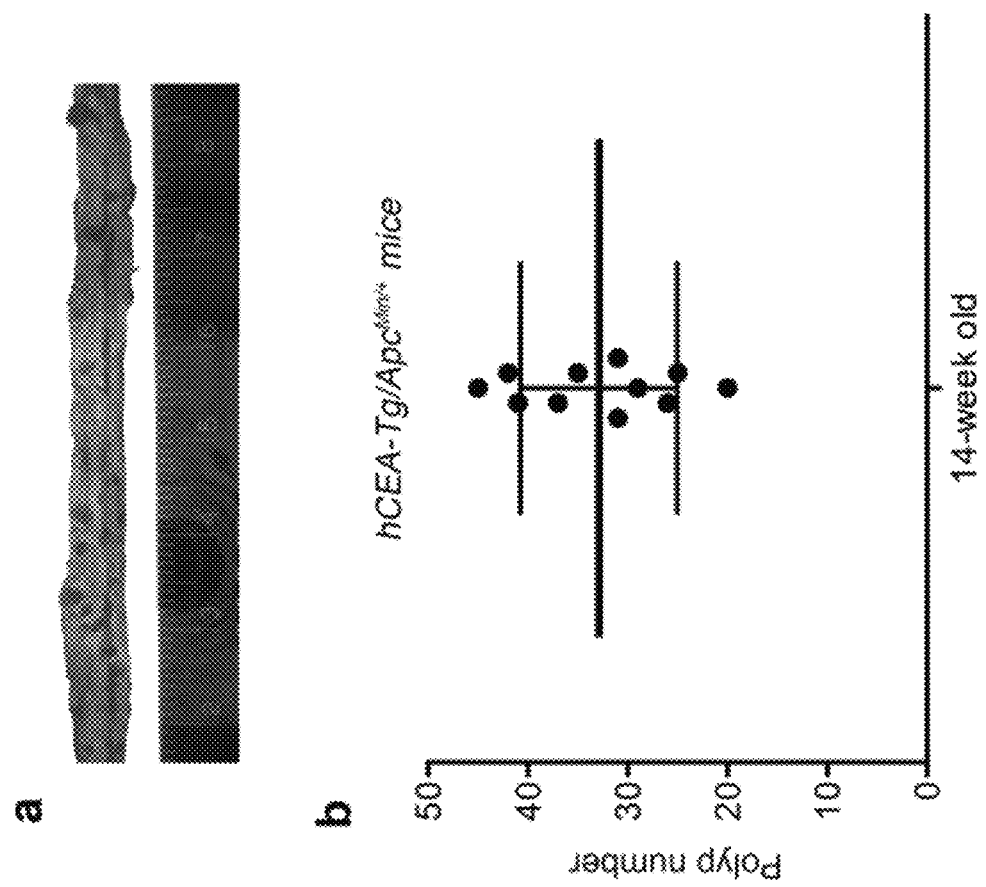
FIG. 6 includes images A and B representing intestinal polyps formation of 14-week old hCEA-Tg/Apc$^{Min/+}$ mice. (A) Methylene blue staining of the small intestine from unimmunized hCEA-Tg/Apc$^{Min/+}$ mice (14-week old). (B) The overall number of intestinal polyps from 14-week old hCEA-Tg/Apc$^{Min/+}$ mice (n=11).

In order to investigate whether the pseudovirus could induce tumor regression in hCEA-Tg/$Apc^{Min/+}$ mice, VLP-hCEA was given, via oral gavage, to hCEA-Tg/$Apc^{Min/+}$ mice at fourteen weeks of age when they had already developed numerous spontaneous polyps along the small intestine (FIG. 6). After three rounds of immunization, with two-week intervals between each immunization (i.e., immunizations at fourteen, sixteen, and eighteen weeks after birth), the anti-tumor efficacy of VLP-hCEA was determined by counting the number of intestinal polyps two weeks after the final immunization (i.e., twenty weeks after birth). As shown in FIG. 1A-C, VLP-hCEA dramatically reduced the overall number of intestinal tumors in hCEA-Tg/$Apc^{Min/+}$ mice. Notably, polyps that were greater than three millimeters in diameter were completely eradicated after immunization (FIGS. 1A and C). Moreover, the splenomegaly, one of the prognostic characteristics that positively correlate with intestinal tumor progression in hCEA-Tg/$Apc^{Min/+}$ mice, was reversed by VLP-hCEA immunization (FIGS. 1D and E). Strikingly, only three doses of VLP-hCEA nearly tripled the lifespan of hCEA-Tg/$Apc^{Min/+}$ mice (FIG. 1F). Consistently, VLP-hCEA treatment also prevented the weight loss in hCEA-Tg/$Apc^{Min/+}$ mice (FIG. 1G).

Figure 8A:
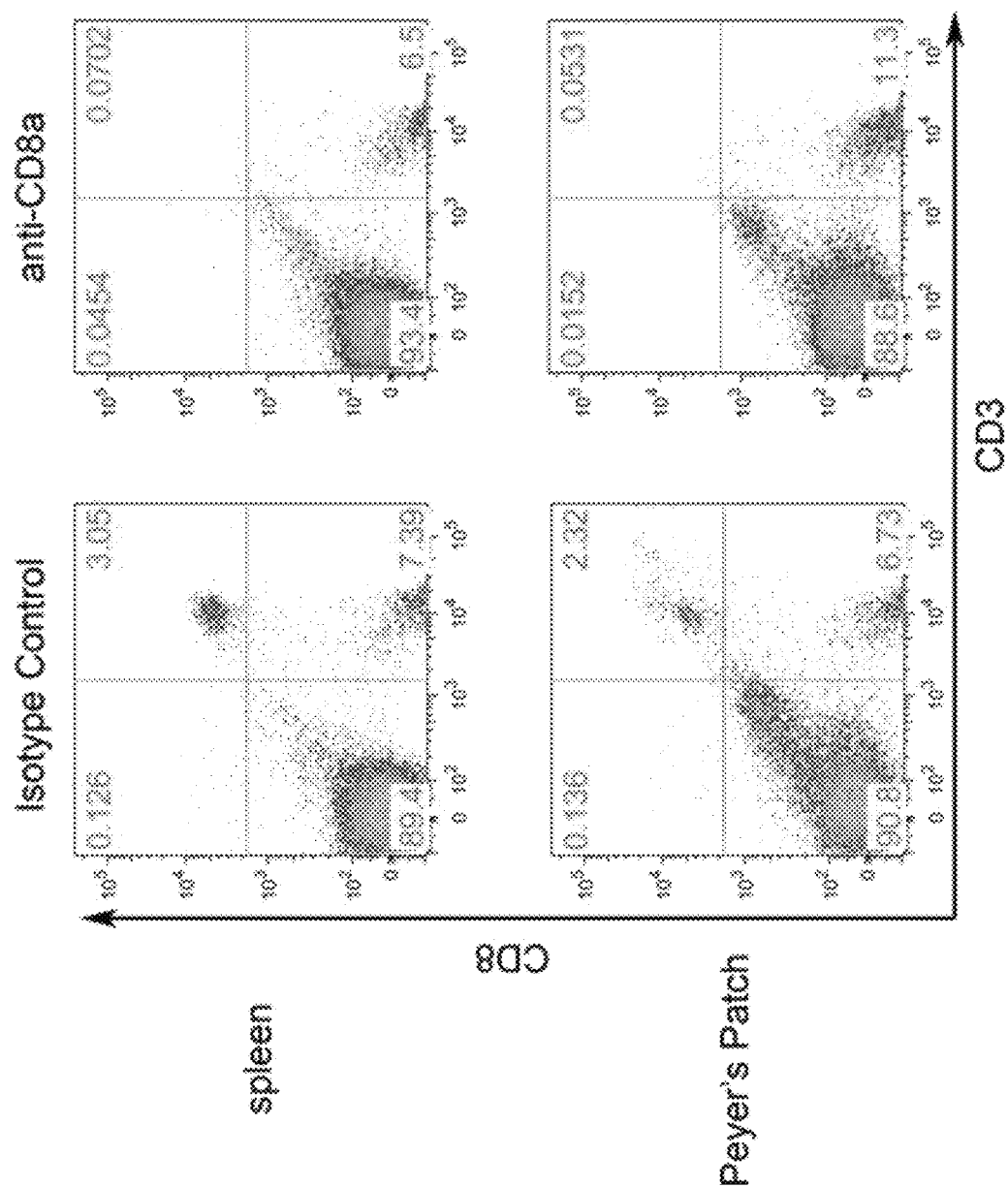
FIG. 8 includes images A through C representing data indicating that CTL response is dispensable for VLP-hCEA-induced tumoricidal effect. (A) Representative flow cytometric analysis of CD8$^+$ T cells in spleens and Peyer's Patches after anti-CD8a neutralizing antibody injection in hCEA-Tg/Apc$^{Min/+}$ mice. (B) The number of intestinal polyps in hCEA-Tg/Apc$^{Min/+}$ mice that were pre-deleted of CD8$^+$ T cells followed by VLP-hCEA immunization. Data are representative of two independent experiments. (C) The intestinal polyp numbers from hCEA-Tg/Apc$^{Min/+}$ mice that were received either control sera (from untreated hCEA-Tg/Apc$^{Min/+}$ mice) or the sera from VLP-hCEA treated (3-dose immunization) hCEA-Tg/Apc$^{Min/+}$ mice. N=10-13 in B and C, ***, p<0.001.
Figure 8B:
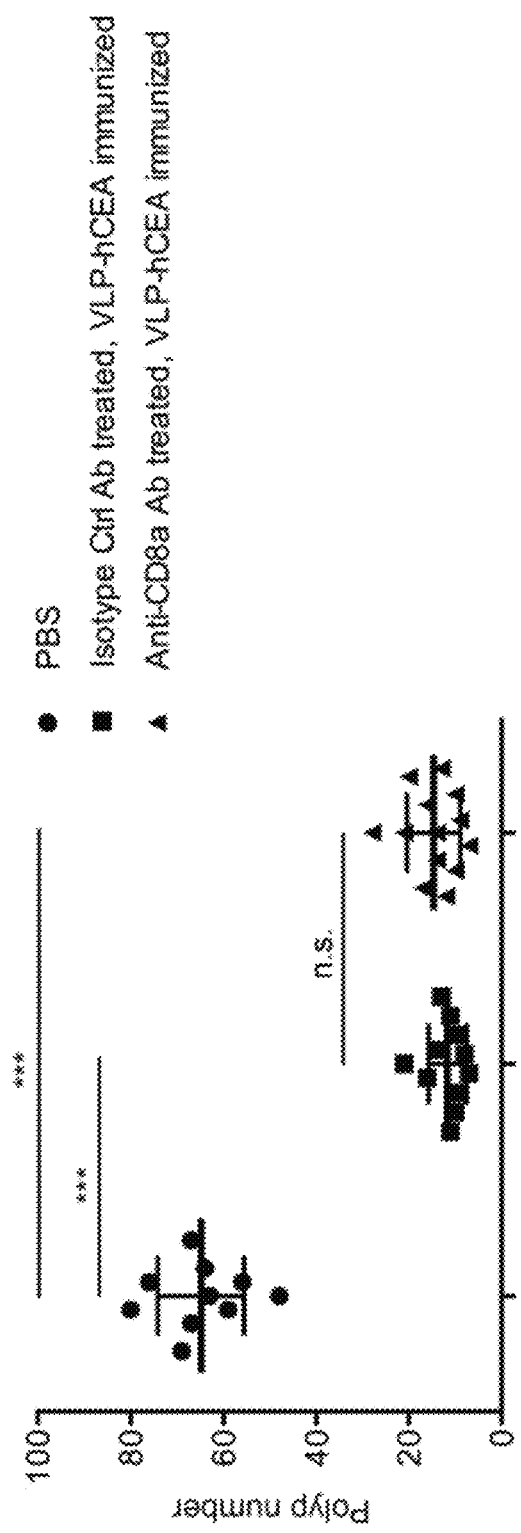
Figure 8C:
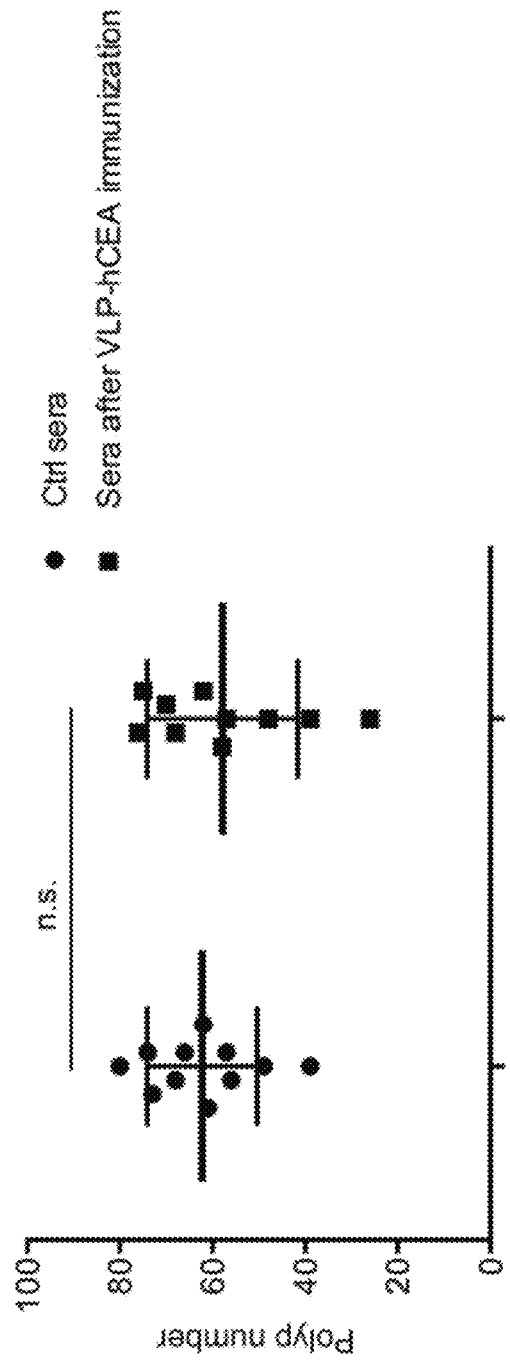

To dissect the mechanism underlying the anti-tumor effect of VLP-hCEA, the adaptive immune responses, in particular the CD8+ T cell response, were investigated. The data indicated that VLP-hCEA immunization induced hCEA specific T and B cell responses (FIG. 6). Surprisingly, however, depleting CD8+ T cells prior to and throughout VLP-hCEA immunization did not affect the anti-tumor efficacy seen in hCEA-Tg/$Apc^{Min/+}$ mice (FIGS. 8A and B). Moreover, the immune sera transferred from VLP-hCEA immunized hCEA-Tg/$Apc^{Min/+}$ mice also failed to reduce tumor numbers in unimmunized hCEA-Tg/$Apc^{Min/+}$ mice (FIG. 8C). These results suggested that VLP-hCEA-elicited cellular and humoral immune responses are dispensable for tumor regression.

Figure 2:
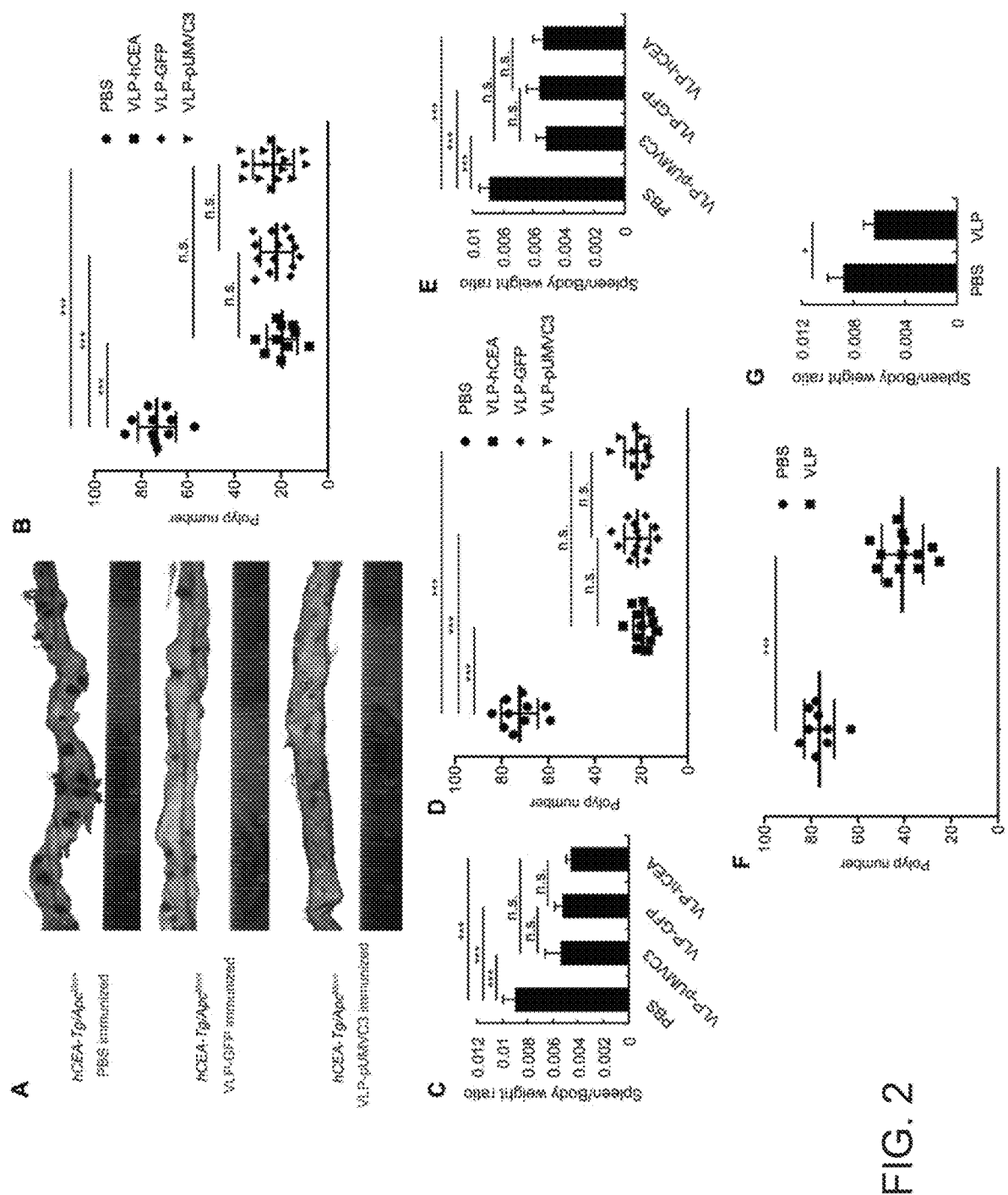
FIG. 2 includes images A through G representing data indicating that PsV eradicated intestinal tumors in hCEA-Tg/Apc$^{Min/+}$ mice independently of hCEA-expression. (A) Methylene blue staining of the small intestines from hCEA-Tg/Apc$^{Min/+}$ mice that were immunized with PBS, VLP-GFP or VLP-pUMVC3 pseudoviruses. (B) The overall numbers of intestinal polyps from hCEA-Tg/Apc$^{Min/+}$ mice (n=10-15) that were immunized as described in A. (C) The ratios of mouse spleen to whole body weight of hCEA-Tg/Apc$^{Min/+}$ mice that were immunized as described in A. (D) Intestinal polyp numbers of Apc$^{Min/+}$ mice (n=10-15) that were immunized with PBS, VLP-hCEA, VLP-GFP or VLP-pUMVC3 pseudoviruses. (E) The ratios of mouse spleen to whole body weight of Apc$^{Min/+}$ mice (n=7) that were immunized as described in D. (F) Intestinal polyp numbers of hCEA-Tg/Apc$^{Min/+}$ mice that were immunized with PBS or VLP (n=9, 13). (G) The ratios of mouse spleen to whole body weight of Apc$^{Min/+}$ mice that were immunized as described in F, n=7.***, p<0.001.
Figure 7:
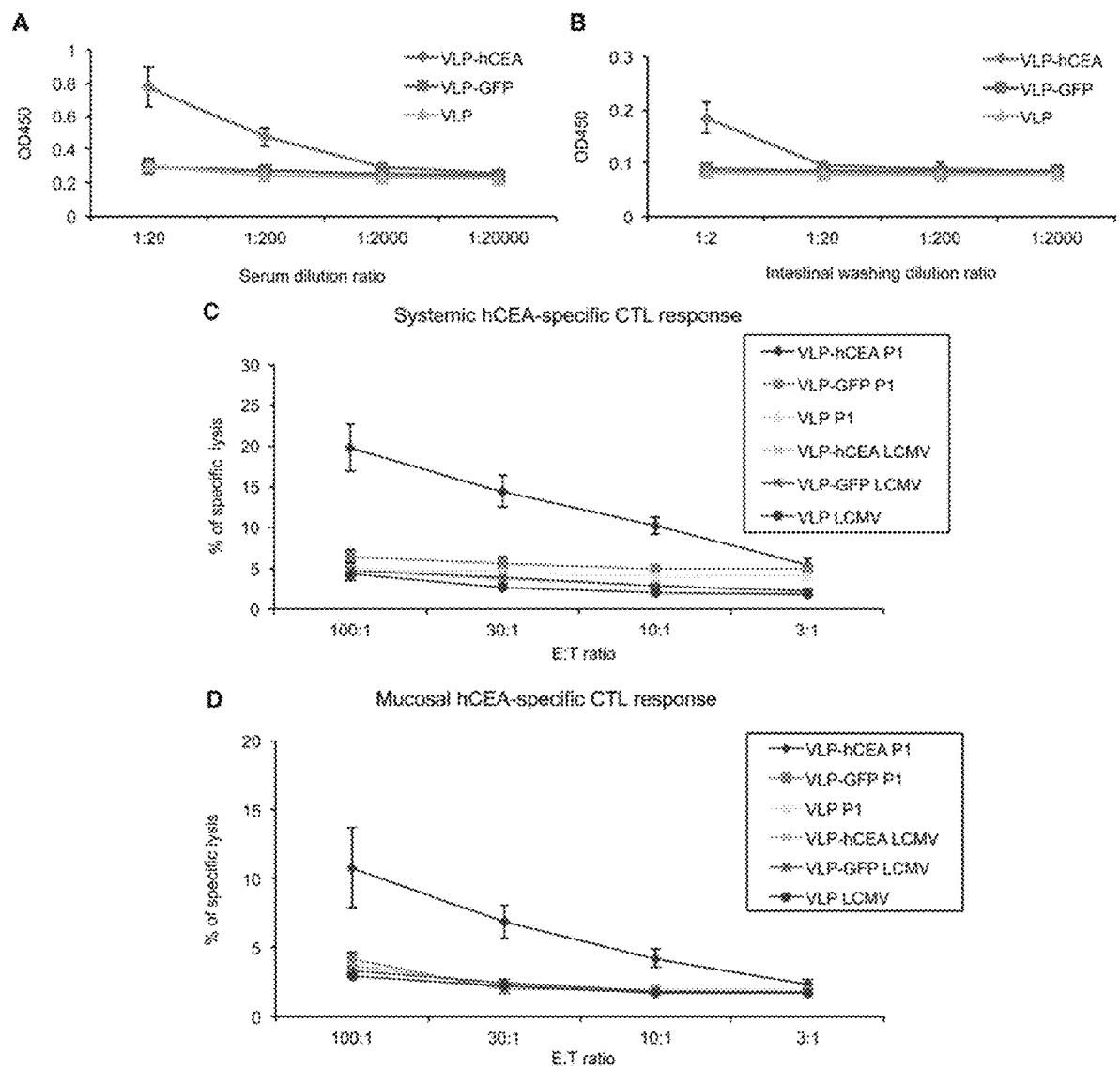
FIG. 7 includes images A through D representing data indicating that VLP-hCEA pseudovirus induces hCEA-specific immunity in hCEA-Tg/Apc$^{Min/+}$ mice. (A,B) The levels of hCEA-specific serum IgG (A) and intestinal IgA (B) after immunization of VLP, VLP-GFP or VLP-hCEA in hCEA-Tg/Apc$^{Min/+}$ mice. Data are shown as OD450 values and are representative of three independent experiments. (C,D) $^{51}$Cr-release assay to determine the splenic or mucosal hCEA-specific CTL responses after VLP, VLP-GFP or VLP-hCEA immunization in hCEA-Tg/Apc$^{Min/+}$ mice. P1: hCEA peptide 526-533, EAQNTTYL (SEQ ID NO: 35); LCMV: control peptide Gp33, KAVYNFATC (SEQ ID NO: 36). Data are representative of three independent experiments.

Intriguingly, in comparison with those hCEA-Tg/$Apc^{Min/+}$ mice that received VLP-hCEA immunization, a similar extent of tumor regression and splenomegaly reduction was unexpectedly found when the mice were treated with a control PsV that contained either a GFP plasmid (VLP-GFP) or an empty pUMVC3 plasmid vector (VLP-pUMVC3) (FIGS. 1 B,C and 2A-C). Notably, only VLP-hCEA induced anti-hCEA specific immunity (FIG. 7). These striking data indicate that neither the expression of hCEA nor generation of hCEA-specific immunity is needed for a PsV-induced tumoricidal effect. To confirm this, experiments were performed to determine if removing hCEA in mice would also have no effect on the tumoricidal effect of VLP-hCEA. Indeed, oral administration of $Apc^{Min/+}$ mice (no hCEA expression) with VLP-hCEA, VLP-GFP, or VLP-pUMVC3 pseudoviruses eradicated the intestinal tumors and reduced splenomegaly to similar levels as found in the VLP-hCEA immunized hCEA-Tg/$Apc^{Min/+}$ mice (FIG. 2D,E). These completely unexpected results suggested that the hCEA-specific adaptive immunity in the host may not be essential for PsV-induced intestinal tumor regression. Interestingly enough, VLP alone (the empty viral shell without any DNA plasmid packaged inside) was also capable of reducing intestinal tumors and splenomegaly in hCEA-Tg/$Apc^{Min/+}$ or $Apc^{Min/+}$ mice, although the extent was only approximately 40% of that induced by PsV (FIG. 2F,G and data not shown). Together, these data indicated that, hCEA-specific immunity is not necessary for PsV-induced tumor eradication. Instead, both the VLP and DNA plasmid packaged inside VLP appear to contribute to the tumoricidal effect in the gut.

Figure 3:
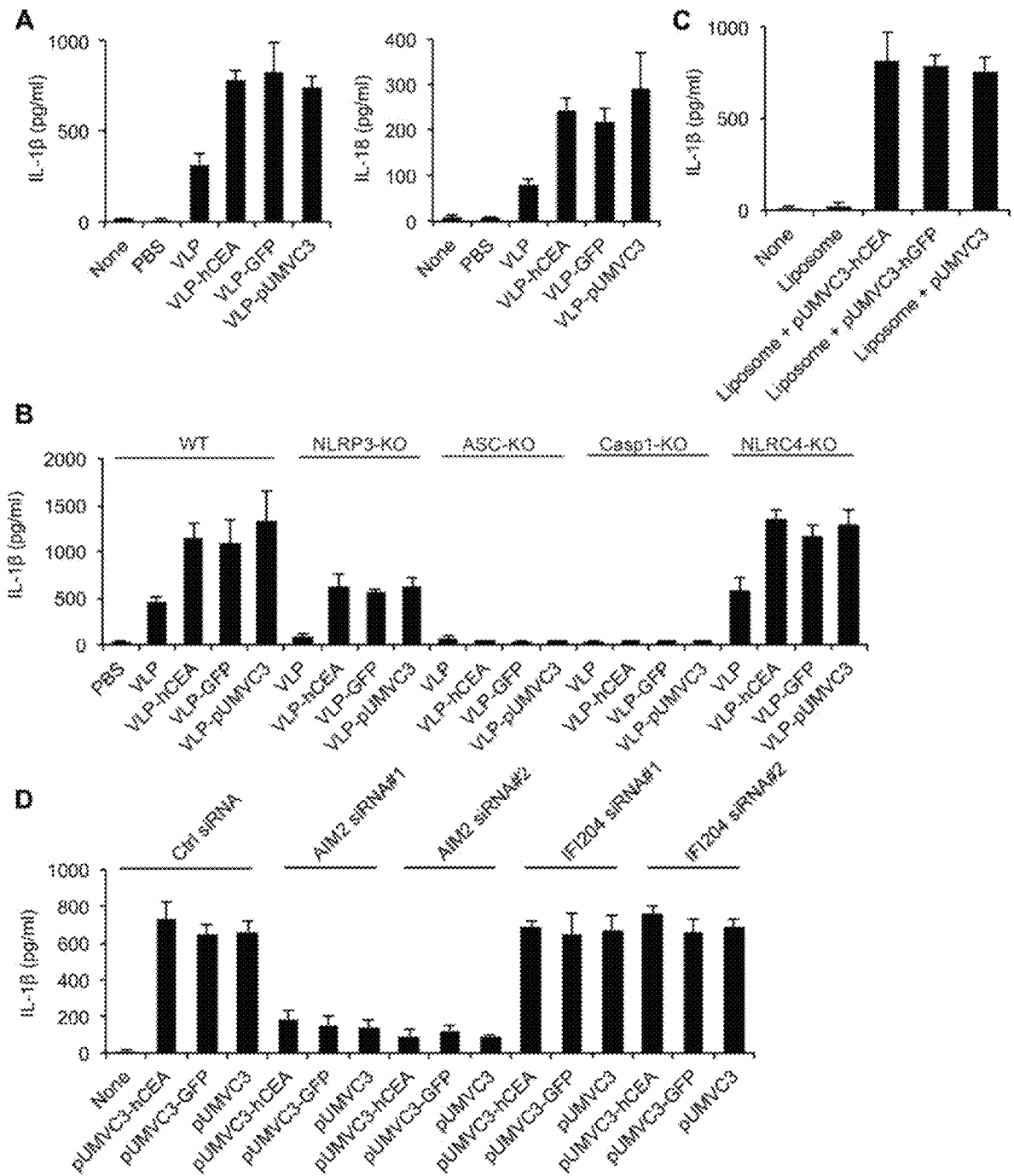
FIG. 3 includes images A through D representing data indicating that VLP and plasmid DNA activates NLRP3 and AIM2 inflammasomes, respectively. (A) The levels of secreted IL-1β (left panel) or IL-18 (right panel) from small intestinal macrophages that were primed with LPS followed by stimulation with indicated stimuli. (B) IL-1β levels from LPS-primed WT, NLRP3-KO, ASC-KO, Casp1-KO or NLRC4-KO immortalized BMDMs that were activated by the stimuli as indicated. (C) IL-1β levels from LPS-primed BMDMs that were stimulated with indicated stimuli. (D) IL-1β levels from LPS-primed WT or AIM2/IFI204 deficient BMDMs that were transfected with DNA plasmids as indicated. All data are representative of at least three independent experiments.
Figure 9:
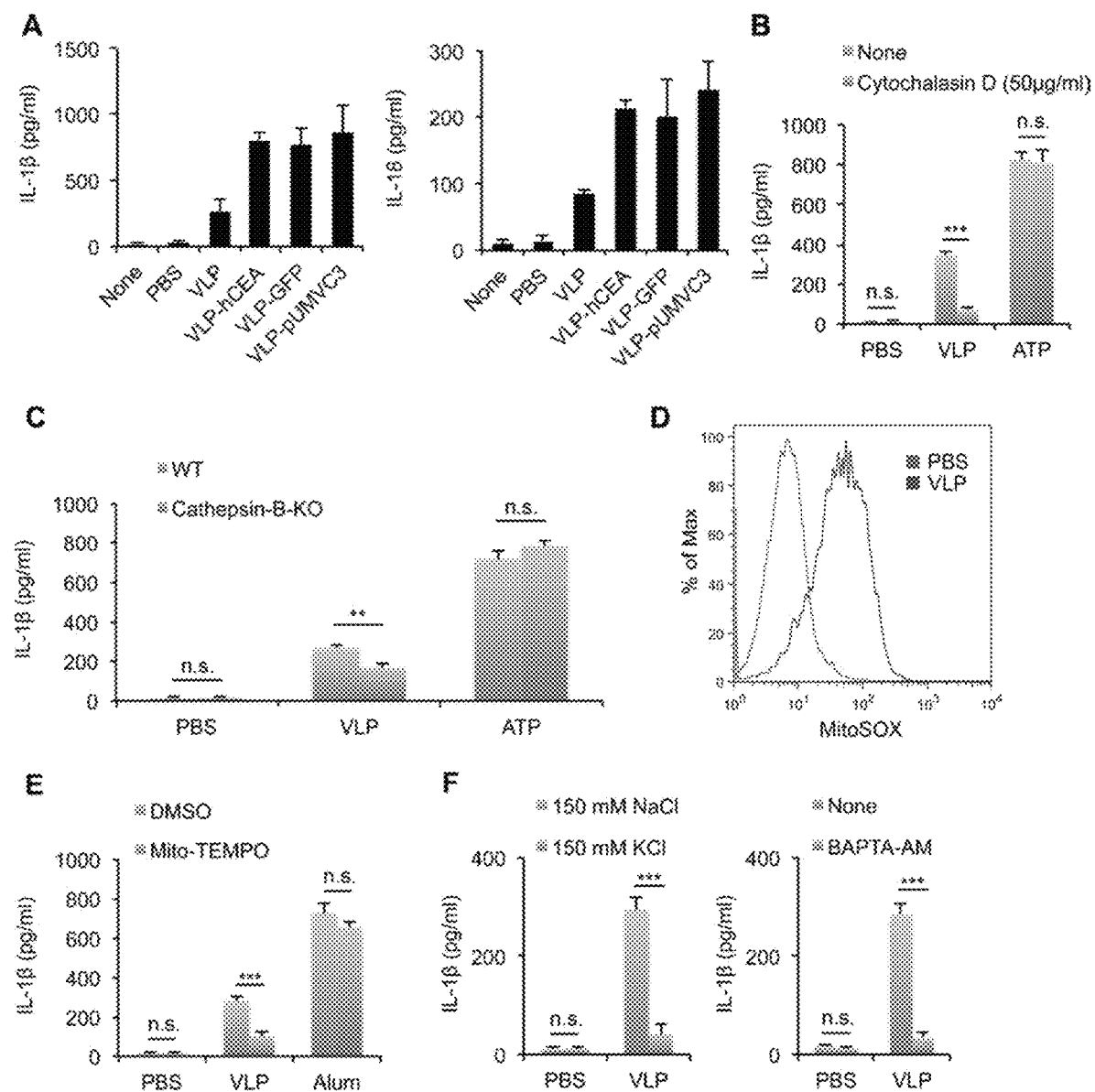
FIG. 9 includes images A through F representing data indicating that VLP activates the NLRP3 inflammasome. (A) The levels of secreted IL-1β (left panel) or IL-18 (right panel) from primary BMDMs that were primed with LPS followed by stimulation with stimuli as indicated. (B) IL-1β levels from LPS-primed BMDMs that were pretreated with cytochalasin D followed by VLP or ATP stimulation. (C) IL-1β levels from LPS-primed immortalized WT or cathepsin-B deficient BMDMs that were stimulated with VLP or ATP. (D) Flow cytometric analysis of MitoSOX in primary WT BMDMs that were treated with PBS or VLP. (E) IL-1β levels from LPS-primed WT BMDMs that were pretreated with DMSO or Mito-TEMPO followed by VLP or Alum stimulation. (F) The effect of potassium and calcium fluxes in IL-1β secretion in response to VLP stimulation in primary WT BMDMs. , p<0.01; *, p<0.001. All data are representative of three independent experiments.
Figure 10:
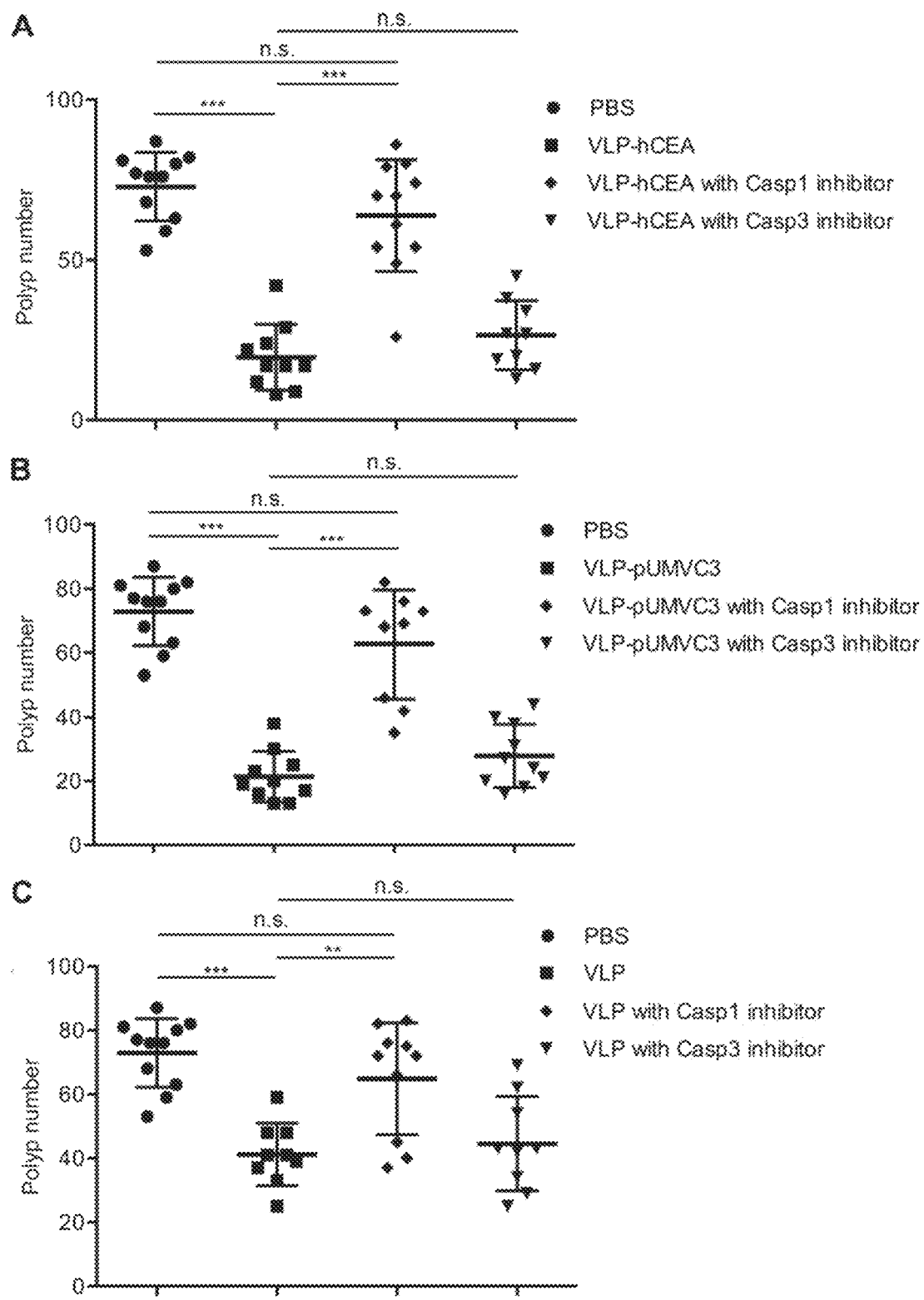
FIG. 10 includes images A through C representing data indicating that Capase-1 mediates the anti-tumor effect of PsV or VLP in Apc$^{Min/+}$ mice. Numbers of Intestinal polyps Apc$^{Min/+}$ mice that were treated with caspase-1 or -3 inhibitors followed by immunization VLP-hCEA (A), VLP-pUMVC3 (B) or VLP (C). N=9-11,***, p<0.001.

In another investigation leading to the present invention, experiments were designed to study the innate immune responses induced by VLP. Macrophages from the small intestines of 14-week old $Apc^{Min/+}$ mice were isolated and then stimulated with VLP, followed by measuring cytokine release 24 hours post-stimulation. Observations showed VLP induced secretions of IL-1β and IL-18 from macrophages (FIG. 3A). APC mutations can breach intestinal integrity, resulting in infiltration of bone marrow-derived mononuclear cells into the gut. Therefore, experiments were conducted to determine if VLP can also induce IL-1β and IL-18 release from bone marrow derived macrophages (BMDMs). Like intestinal macrophages, observations showed a similar response after VLP treatment (FIG. 9A) in BMDMs. VLP-induced IL-1β and IL-18 release was largely dependent on NLRP3 inflammasome because macrophages deficient in NLRP3, ASC, or Caspase-1/11 abolished this effect (FIG. 3B). Mechanistically, it was determined that VLP required phagocytic uptake and lysosomal cathepsin B activity to activate inflammasome (FIGS. 9B and C). Moreover, VLP stimulation also induced mitochondrial reactive oxygen species (mtROS) production in myeloid cells (FIG. 9D), and blockade of mtROS inhibited VLP-induced inflammasome activation (FIG. 9E). Additionally, consistent with many known NLRP3 agonists, the inhibition of ion fluxes also impaired VLP-induced inflammasome activation (FIG. 9F). These data collectively indicated that VLP can engage NLRP3 inflammasome to activate caspase-1 and promote pro-IL-1β processing.

Interestingly, it was determined that PsV, similar to VLP, also triggered release of inflammasome dependent cytokines from myeloid cells (FIG. 3A and FIG. 9A), but with a higher extent. Because PsV and VLP have equal amounts of bovine papillomavirus L1 protein, it was reasoned that the DNA plasmid packaged inside PsV may also contribute to IL-1β production after PsV stimulation. In support of this notion, deficiency in NLRP3 almost completely blocked VLP-induced IL-1β release whereas only partially impaired PsV-induced IL-1β secretion (FIG. 3B). As ASC or Caspase-1 deficiency completely abolished VLP- or PsV-induced IL-1β secretion (FIG. 3B), it is conceivable that the DNA plasmid packaged inside VLP was sensed via an NLRP3-independent but ASC/Caspase-1-dependent pathway. To further confirm that pUMVC3 plasmid alone can induce IL-1β secretion, liposomes were utilized to transfect macrophages with pUVMC3-hCEA, pUMVC3-GFP or pUMVC3 plasmids. These plasmids triggered caspase-1 activation and secretion of IL-1β, in the absence of VLP (FIG. 3C). To further identify the sensor that detects PsV DNA, small interference RNA (siRNA) was used to knock down AIM2 and IFI204, which were previously shown to sense cytosolic and nuclear DNA, respectively. Although knocking down of IFI204 had minimal effect, ablating AIM2 expression almost completely abolished DNA plasmid-induced IL-1β release (FIG. 3D), suggesting that DNA plasmid inside PsV activates the AIM2 inflammasome. Taken together, the results indicated that VLP activates the NLRP3 inflammasome whereas PsV induces more potent inflammasome activation by engaging both NLRP3 and AIM2.

Figure 11:
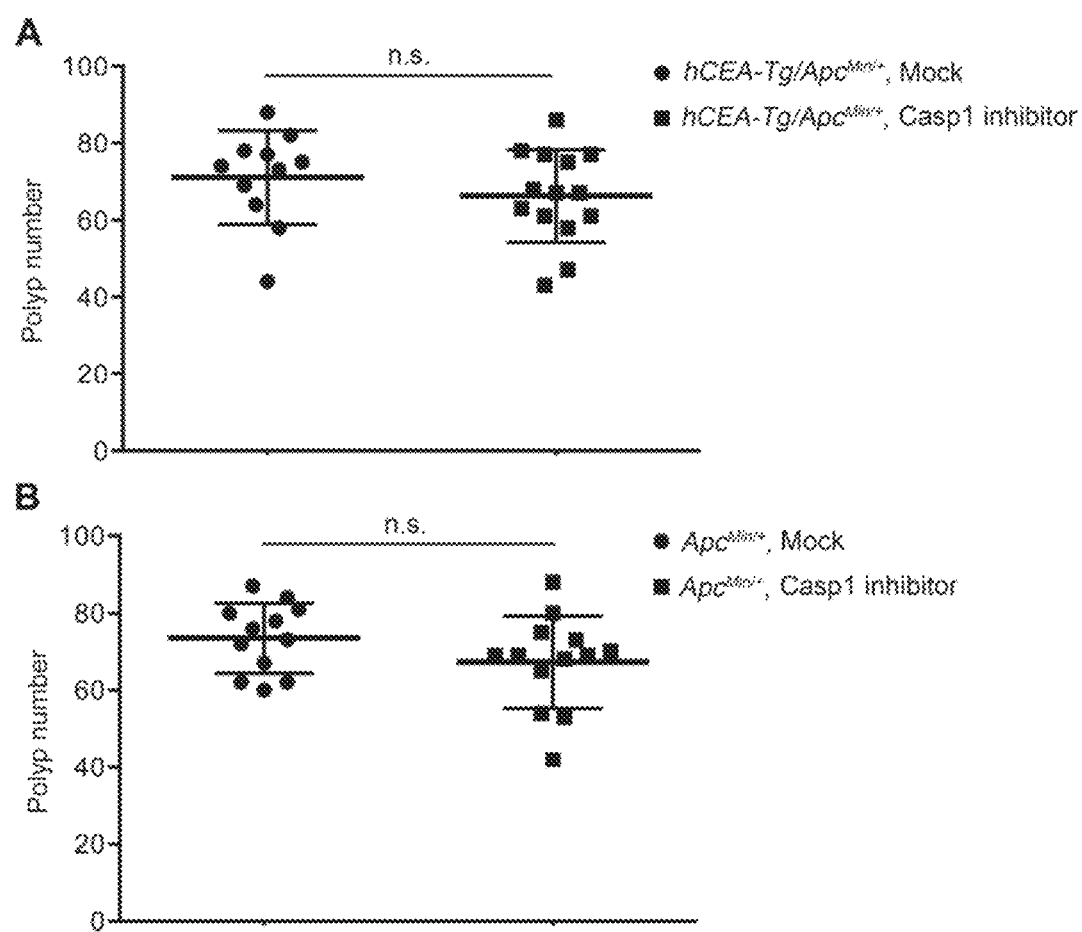
FIG. 11 includes images A and B representing data indicating that Capase-1 does not affect the intestinal tumorigenesis in unimmunized Apc$^{Min/+}$ mice. Numbers of intestinal polyps in unimmunized hCEA-Tg/Apc$^{Min/+}$ (A) or Apc$^{Min/+}$ (B) mice that were treated with caspase-1 inhibitor. N=11-14.

As PsV induces potent inflammasome activation, which positively correlates with a remarkable anti-tumor efficacy, it was reasoned that the extent of PsV-induced caspase-1 activation and subsequent IL-1β/IL-18 release might be responsible for the anti-tumor effect induced by PsV immunization. As caspase-1 is relevant to generating bioactive IL-1β and IL-18, another investigation leading to the present invention was performed to study whether inhibiting caspase-1 may affect the tumoridical effect of PsV in the gut. Indeed, intraperitoneal (i.p.) injection of ZYVAD-FMK (SEQ ID NO: 37), a caspase-1 inhibitor, prior to PsV or VLP immunization abolished the tumoridical effect seen in hCEA-Tg/$Apc^{Min/+}$ or $Apc^{Min/+}$ mice. In contrast, inhibiting caspase-3 had little effect (FIG. 4A-C and FIG. 10). Notably, caspase-1 inhibition did not affect the overall intestinal tumor load or size in unimmunized hCEA-Tg/$Apc^{Min/+}$ or $Apc^{Min/+}$ mice (FIG. 11).

Figure 12:
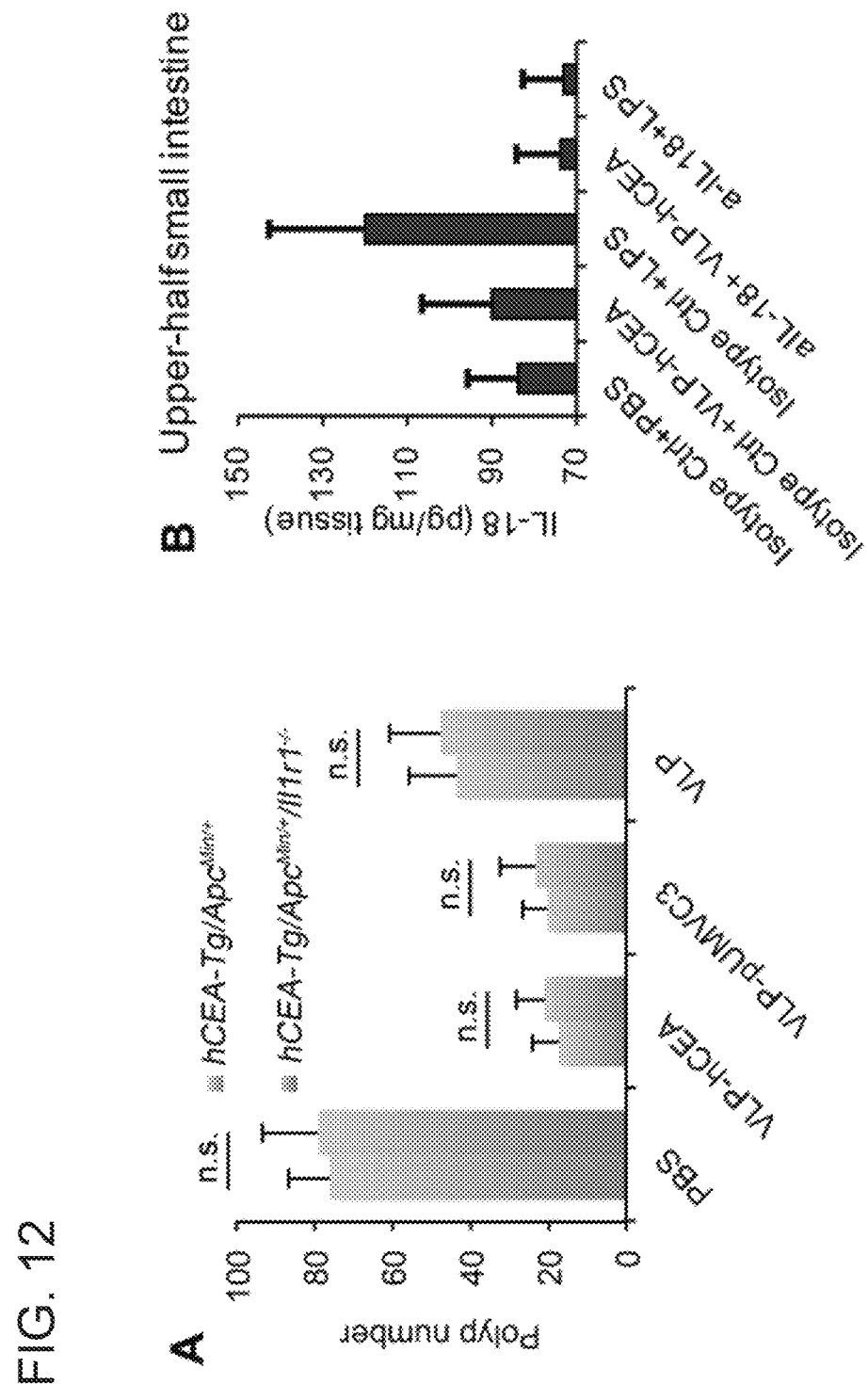
FIG. 12 includes images A through D representing data indicating that IL-1 and IL-18 are dispensable for the PsV-induced anti-tumor effect. (A) Numbers of intestinal polyps in hCEA-Tg/Apc$^{Min/+}$ or hCEA-Tg/Apc$^{Min/+}$/Il-1r1$^{-/-}$ mice that were immunized with PsV or VLP as indicated. n=10 or 15 per group. (B, C) Efficacy of IL-18 neutralization. Anti-mouse IL-18 neutralizing antibody or control antibody (rat IgG1) were given to Apc$^{Min/+}$ mice by i.p. (intraperitoneal injection) (200 μg/dose) on days −1 and day 1 of PsV immunization. Mice were sacrificed at day 2. In control group, LPS was given to mice i.p. (200 μg/mouse) at day 2 and mice were sacrificed 6 hours after injection. Whole small intestines were collected and divided into 2 parts: upper half (B) and lower half (C). IL-18 concentrations were measured by ELISA and calculated as pg/mg tissue. Data are representative of two independent experiments and shown as mean±SD. n=3 in each group. (D) Numbers of intestinal polyps of hCEA-Tg/Apc$^{Min/+}$ mice that were pretreated with either control or anti-IL-18 neutralizing antibody followed by immunization with PsV or VLP as indicated. n=10 or 14 per group.
Figure 12:
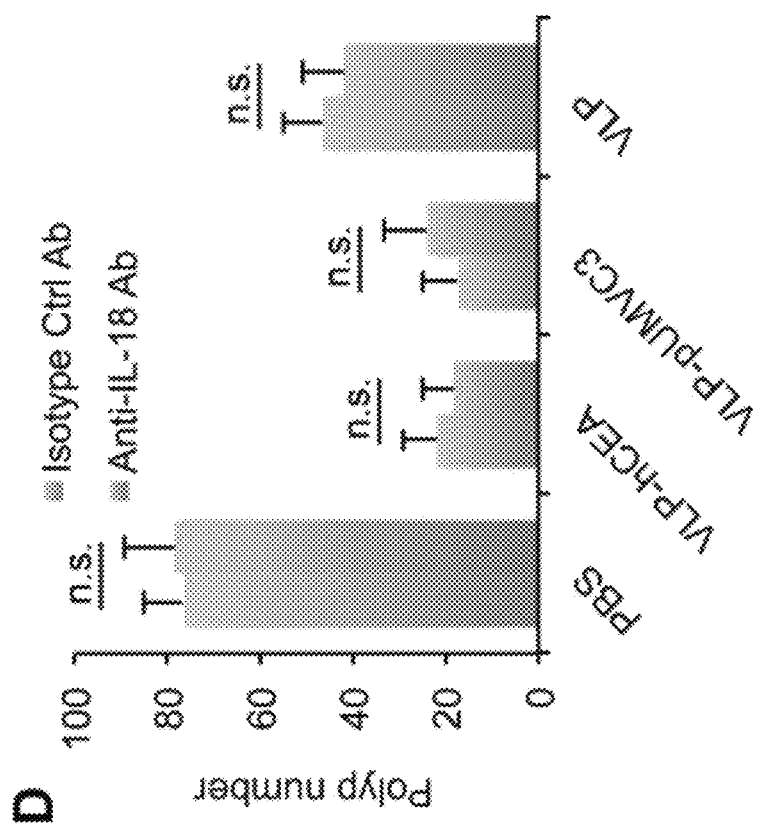
Figure 12:
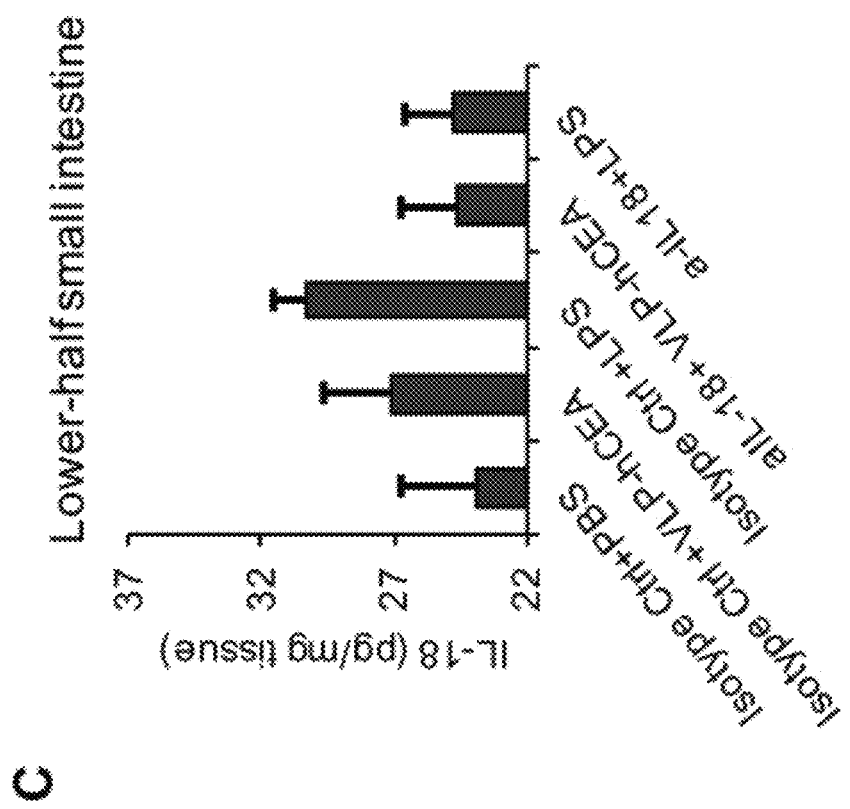

To further investigate the molecular mechanism underlying caspase-1-mediated tumoricidal effect, experiments were performed to test whether IL-1β and IL-18, two downstream cytokines of caspase-1, contributed to PsV-induced tumor regression. IL-1β appeared to be dispensable for eradicating intestinal tumors because genetic ablation of type-I IL-1 receptor (IL-1RI) in hCEA-Tg/$Apc^{Min/+}$ mice did not compromise the anti-tumor efficacy of PsV (FIG. 12A). IL-18 possesses anti-tumor effect, at least partially via regulating IFN-γ, STAT1 and IL-22 bind protein (IL-22BP). However, the blockade of IL-18 signaling by neutralizing antibodies, which effectively reduced gut IL-18 levels (FIGS. 7B and C), only had minimal influence on the tumoricidal effect of PsV in hCEA-Tg/$Apc^{Min/+}$ mice (FIG. 12D). Together, these results indicated that caspase-1-mediated non-IL-1/IL-18 pathway(s) is likely to drive PsV-induced tumor regression.

Figure 4:
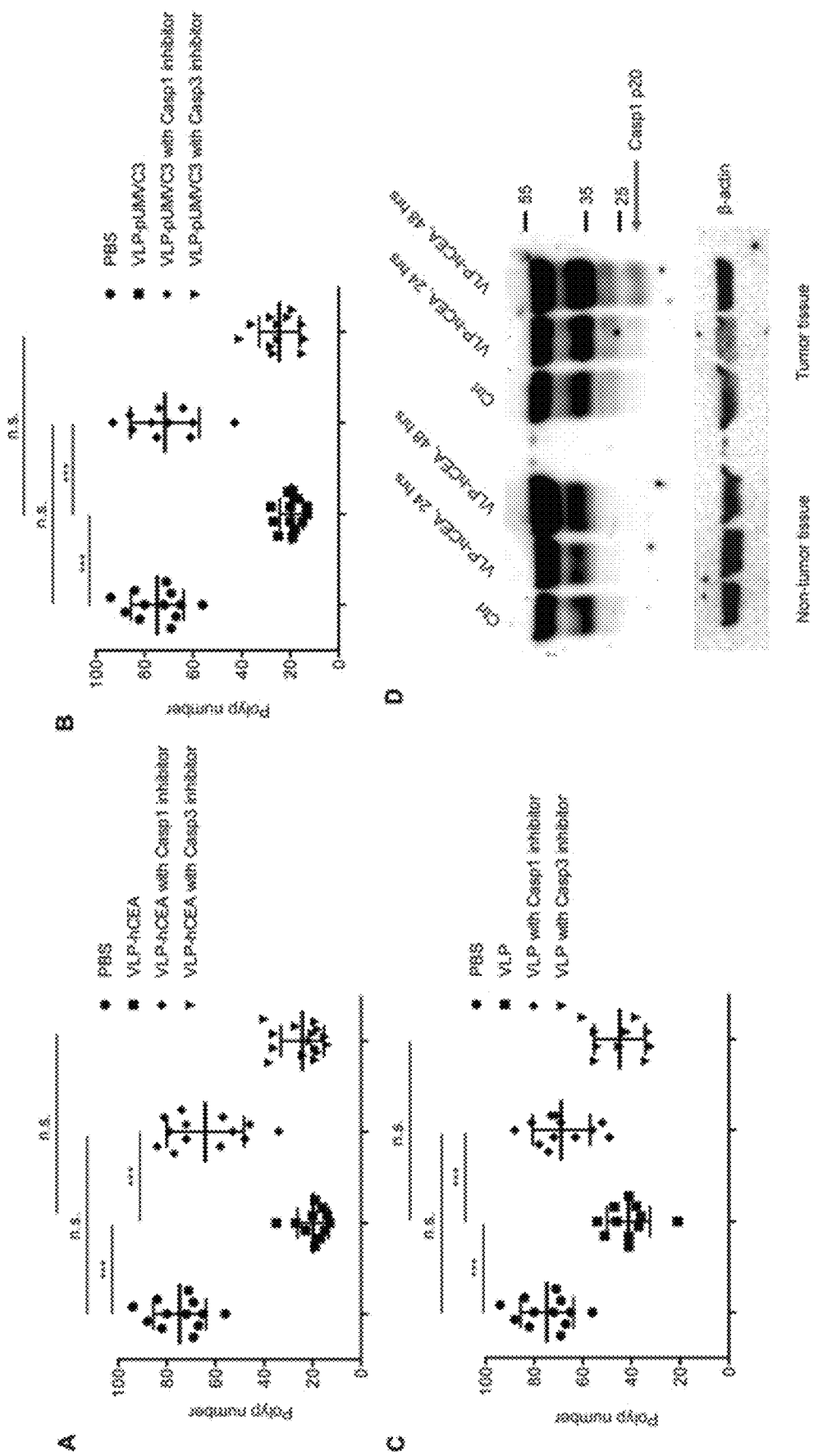
FIG. 4 includes images A through J representing data indicating that PsV or VLP-induced tumoricidal effect in the gut is mediated by caspase-1. (A-C) Intestinal polyp numbers of hCEA-Tg/Apc$^{Min/+}$ mice (n=12-15) that were pretreated with caspase-1 or -3 inhibitors followed by immunization VLP-hCEA (A), VLP-pUMVC3 (B) or VLP (C). , p<0.01; *, p<0.001. (D) 14-week old Apc$^{Min/+}$ mice were immunized (via oral gavage) with VLP-hCEA or PBS control. 24 and 48 hours later, mice were killed and intestinal tissues were collected and separated as non-tumor or tumor tissues. Cellular proteins were extracted and immunoblotted for Caspase-1 or β-actin. (E, F) 14-week old Apc$^{Min/+}$ mice were immunized (via oral gavage) with VLP-GFP. 48 hours post immunization, the polyps of small intestines were collected and stained with anti-EpCAM, anti-GFP antibody, and anti-F4/80 antibodies, respectively. Arrows indicate cells with colocalization of EpCAM/GFP or F4/80/GFP. (G, H) 14-week old Apc$^{Min/+}$ mice were immunized (via oral gavage) with VLP-hCEA. 48 hours post immunization, the polyps of small intestines were collected and stained with anti-EpCAM, anti-F4/80 antibodies and FAM-FLICA-Casp1 probe, respectively. Arrows indicate cells with colocalization of EpCAM/FLICA or F4/80/FLICA. (I, J) 14-week old Apc$^{Min/+}$ mice were immunized (via oral gavage) with VLP-hCEA. 48 hours post immunization, the polyps of small intestines were collected and co-stained with anti-EpCAM (I) or anti-F4/80 (J) antibodies and TUNEL, respectively. Arrows indicate dying intestinal tumor cells or macrophages, evidencing the capability of inducing pyroptosis of macrophages in tumors.
Figure 4E:
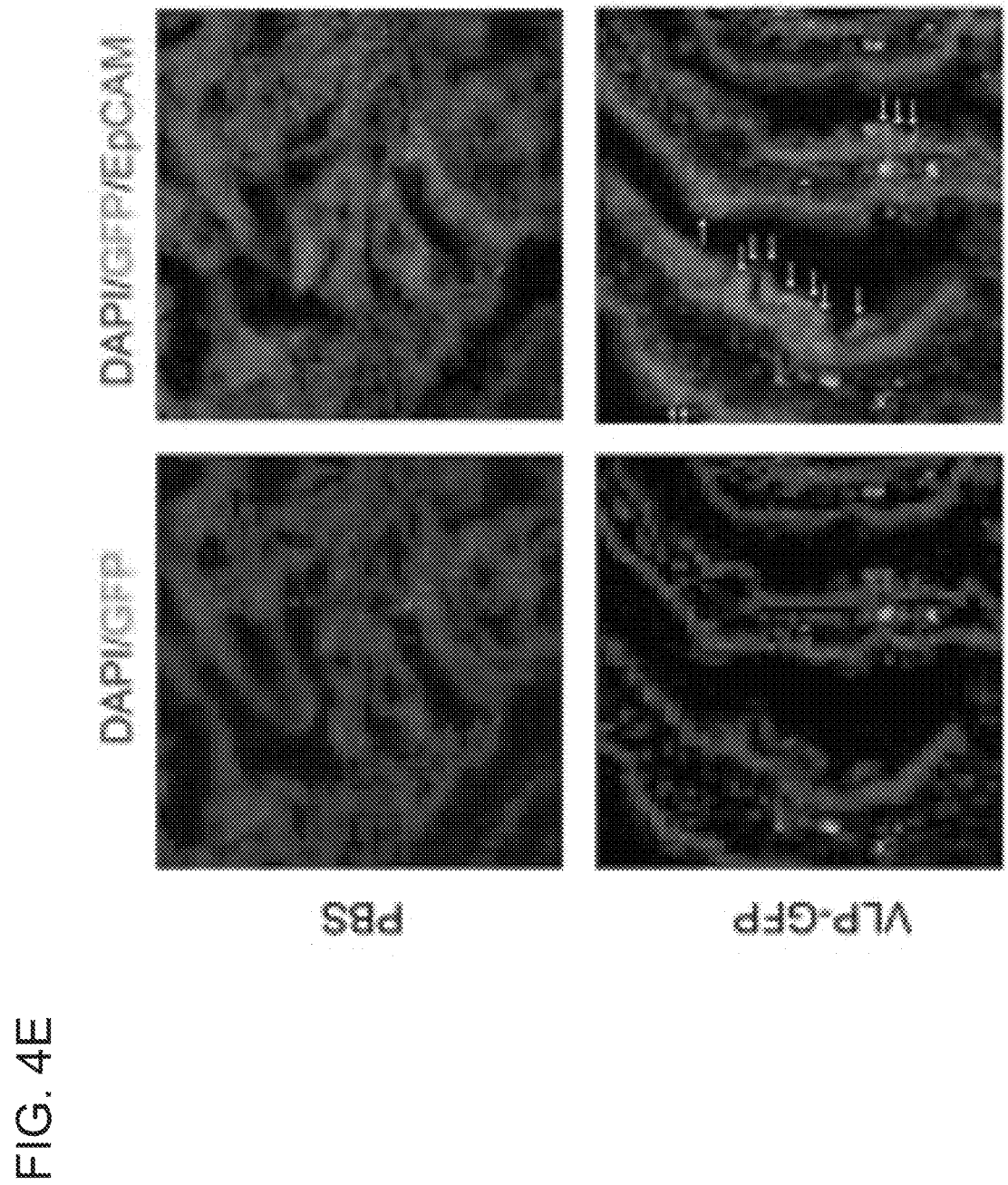
Figure 4F:
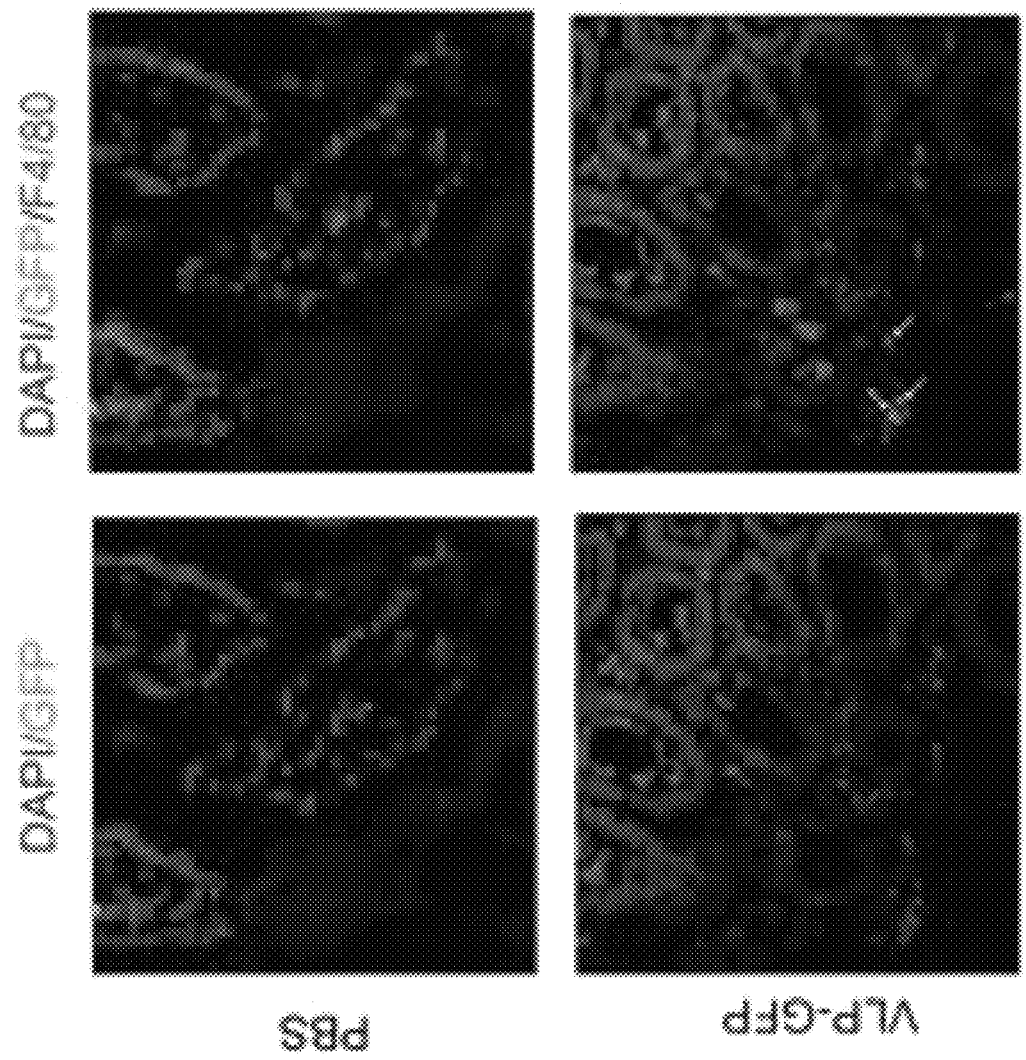
Figure 4H:
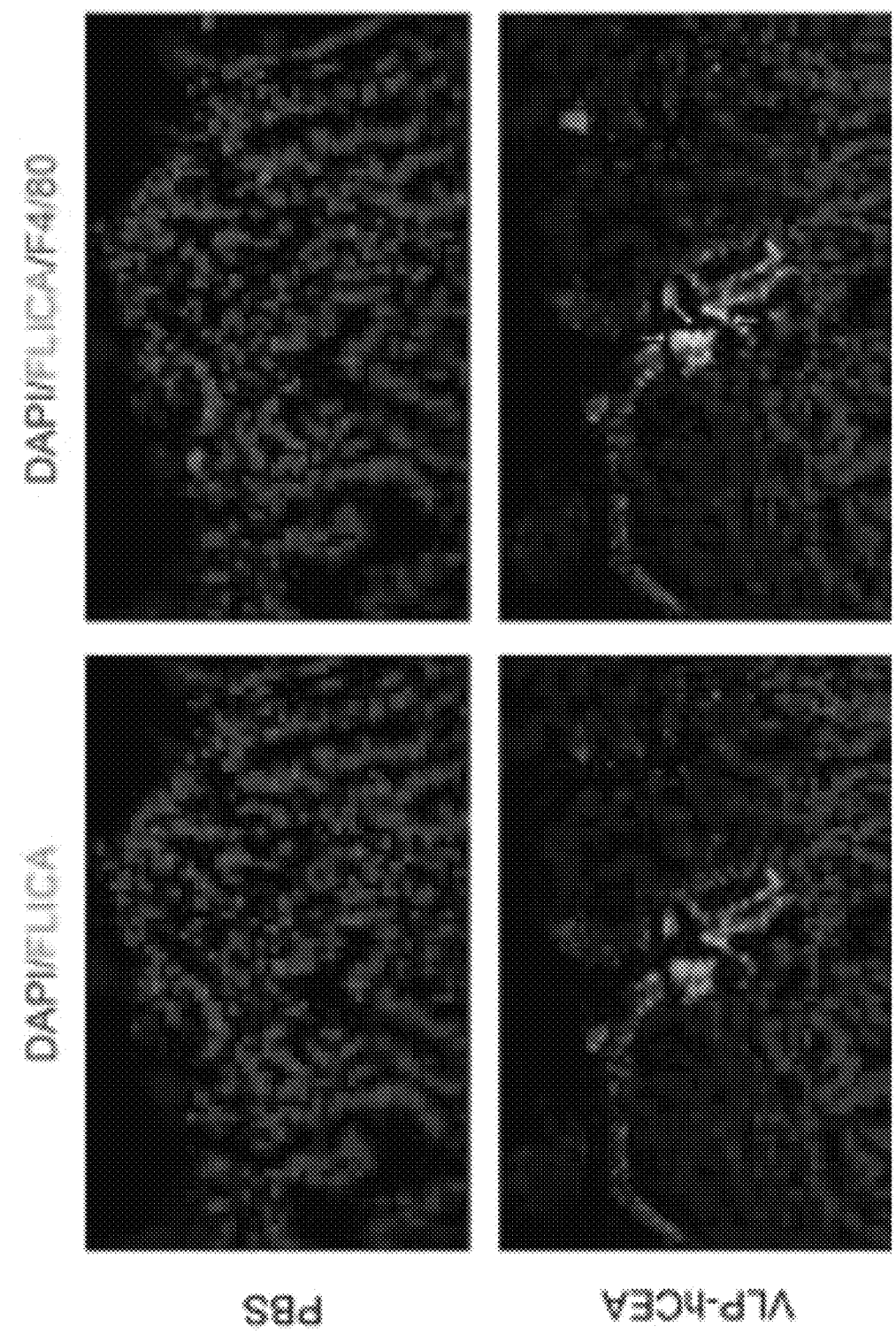
Figure 4I:
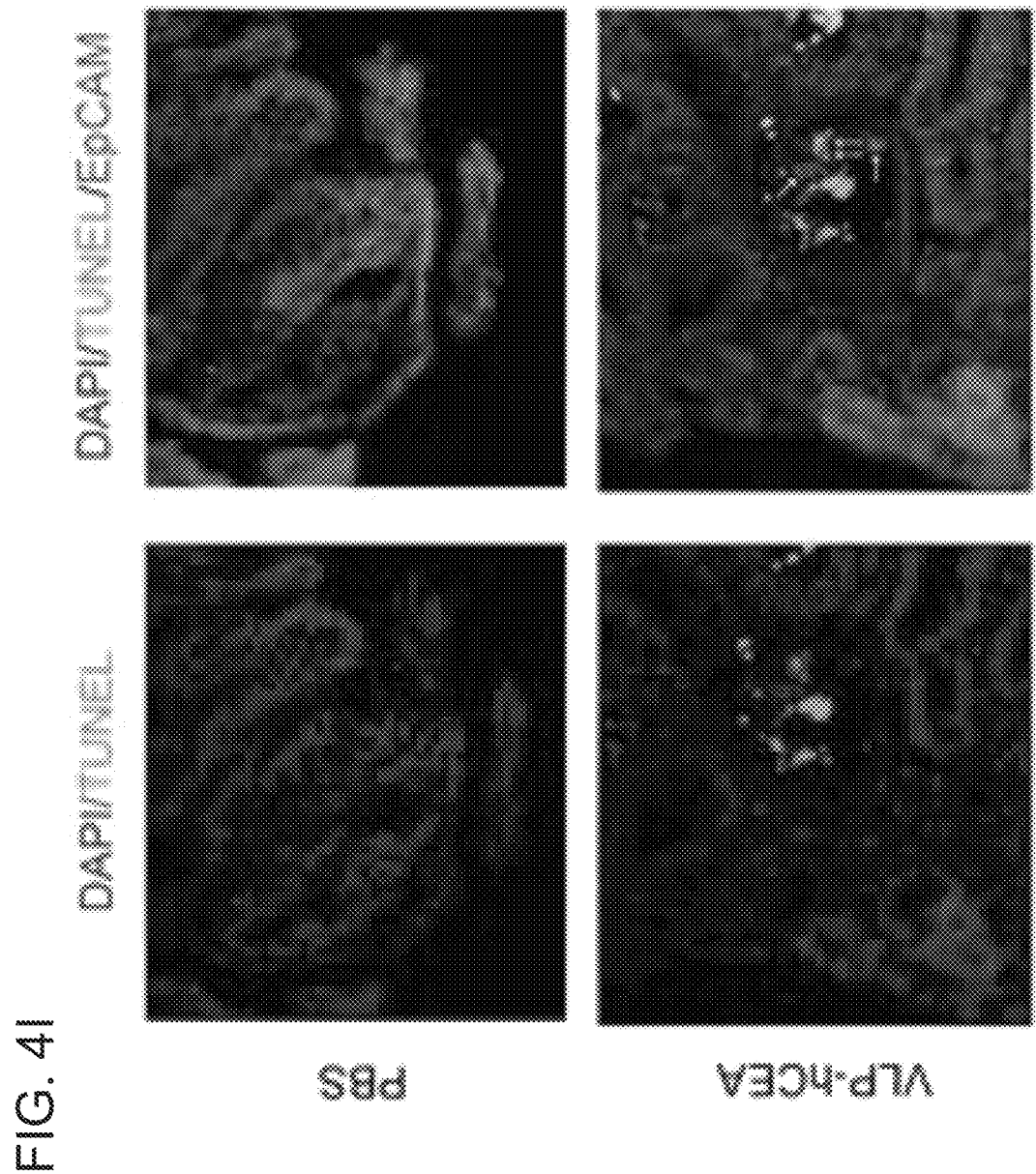
Figure 4J:
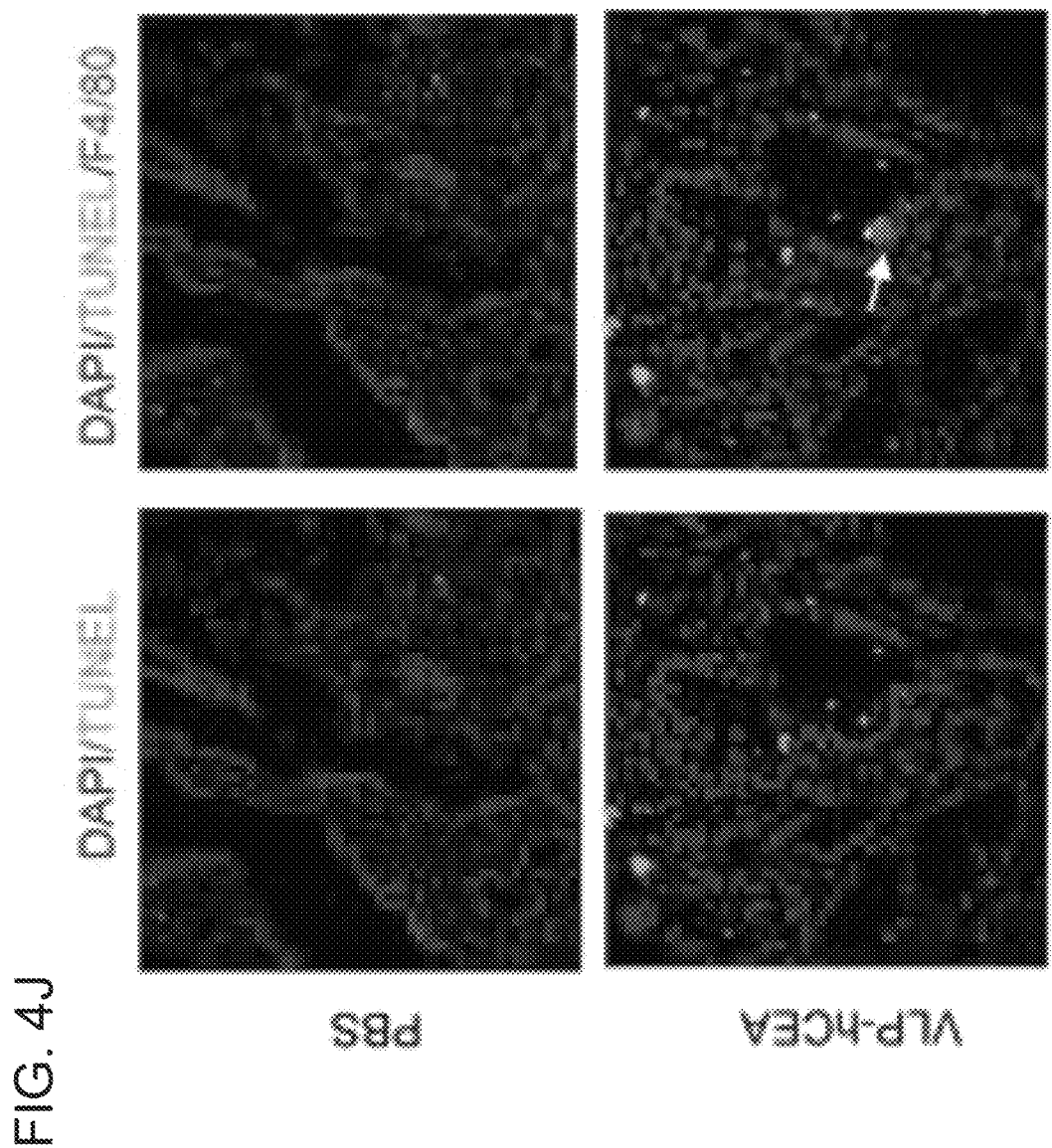

Caspase-1 is known to mediate an inflammatory form of cell death, named pyroptosis. Therefore, an experiment was conducted to determine whether PsV could directly induce intestinal tumor cell death via activating caspase-1. To this end, 14-week old $Apc^{Min/+}$ mice were orally gavaged with a single dose of VLP-GFP and the intestinal tumor and non-tumor tissues were analyzed 24 and 48 hours post immunization. As shown in FIG. 4D, PsV induced pro-caspase-1 processing (p20 fragment) only in tumor tissues, which was more pronounced 48 hours after immunization. In line with this notion, immunofluorescent staining was performed that confirmed that PsV indeed infected intestinal tumor cells in $Apc^{Min/+}$ mice in vivo (FIG. 4E). As expected, PsV was also taken up by intestinal macrophages (FIG. 4F). Importantly, PsV-infected intestinal tumor cells and macrophages had active caspase-1 48 hours after oral gavage immunization, suggesting a rapid ongoing pyroptosis in vivo which was not observed in the PBS treated group (FIG. 4D,G,H). Consistently, a significantly increased number of dying intestinal tumor cells and macrophages were observed by TUNEL staining 48 hours after PsV immunization (FIG. 4I, J), evidencing the capability of inducing pyroptosis of macrophages in tumors. Briefly, FIG. 4 represents data indicating that VLP-hCEA immunization altered the intestinal tumor microenvironment by deleting tumor-associated macrophages or other cells that promote tumor growth, thereby inducing tumor regression.

Figure 13:
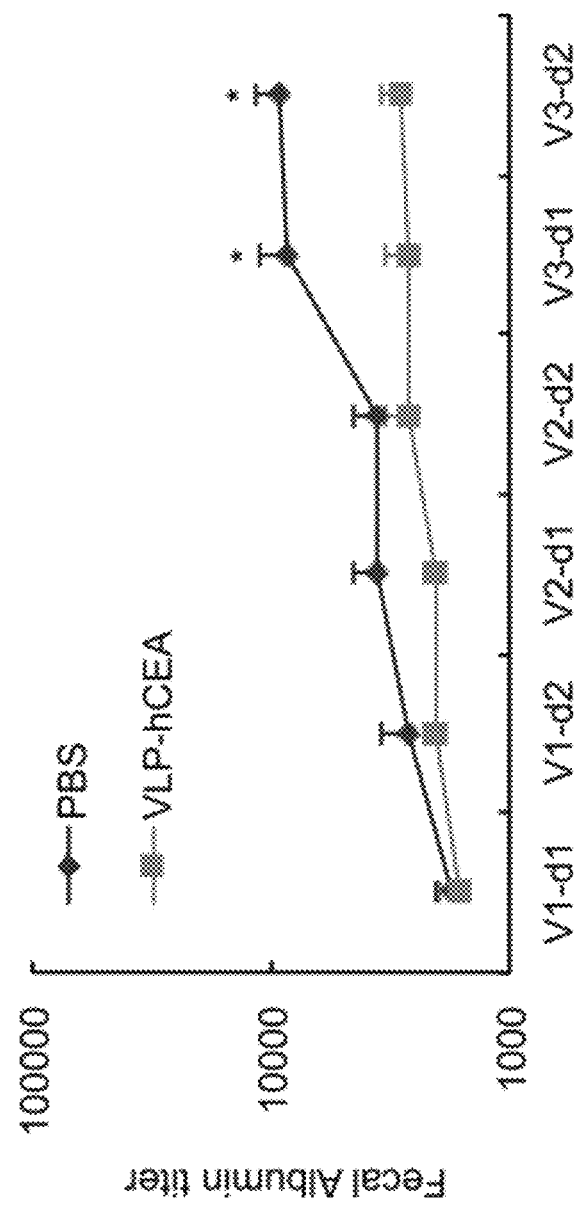
FIG. 13 represents data indicating that PsV does not worsen the gut barrier function in hCEA-Tg/Apc$^{Min/+}$ mice. Time lapse [1 or 2 days (d1 or d2) after each treatment (V1, V2, and V3)] measurement of fecal albumin levels from hCEA-Tg/Apc$^{Min/+}$ mice that were treated with either PBS or VLP-hCEA.

Induction of intestinal tumor cell death by PsV immunization raised the concern whether PsV might compromise intestinal barrier function, leading to increased translocation of gut microbes that promote inflammation and development of inflammatory bowel disease. Therefore, it was next investigated whether the gut permeability was compromised after PsV or VLP immunization. To this end, the levels of fecal albumin, an indicator for gut permeability, were quantified before and after PsV or VLP oral gavage immunization. As shown in FIG. 13, no significant changes in fecal albumin levels were found between VLP-hCEA and PBS treated mice during the first two immunizations, indicating that the intestinal barrier function is not affected by vaccination. Interestingly, VLP-hCEA treatment eventually led to a better preservation of gut integrity relative to PBS-treated mice (FIG. 13), which positively correlates with the reduced tumor formation and enhanced survival of after immunization.

Figure 14:
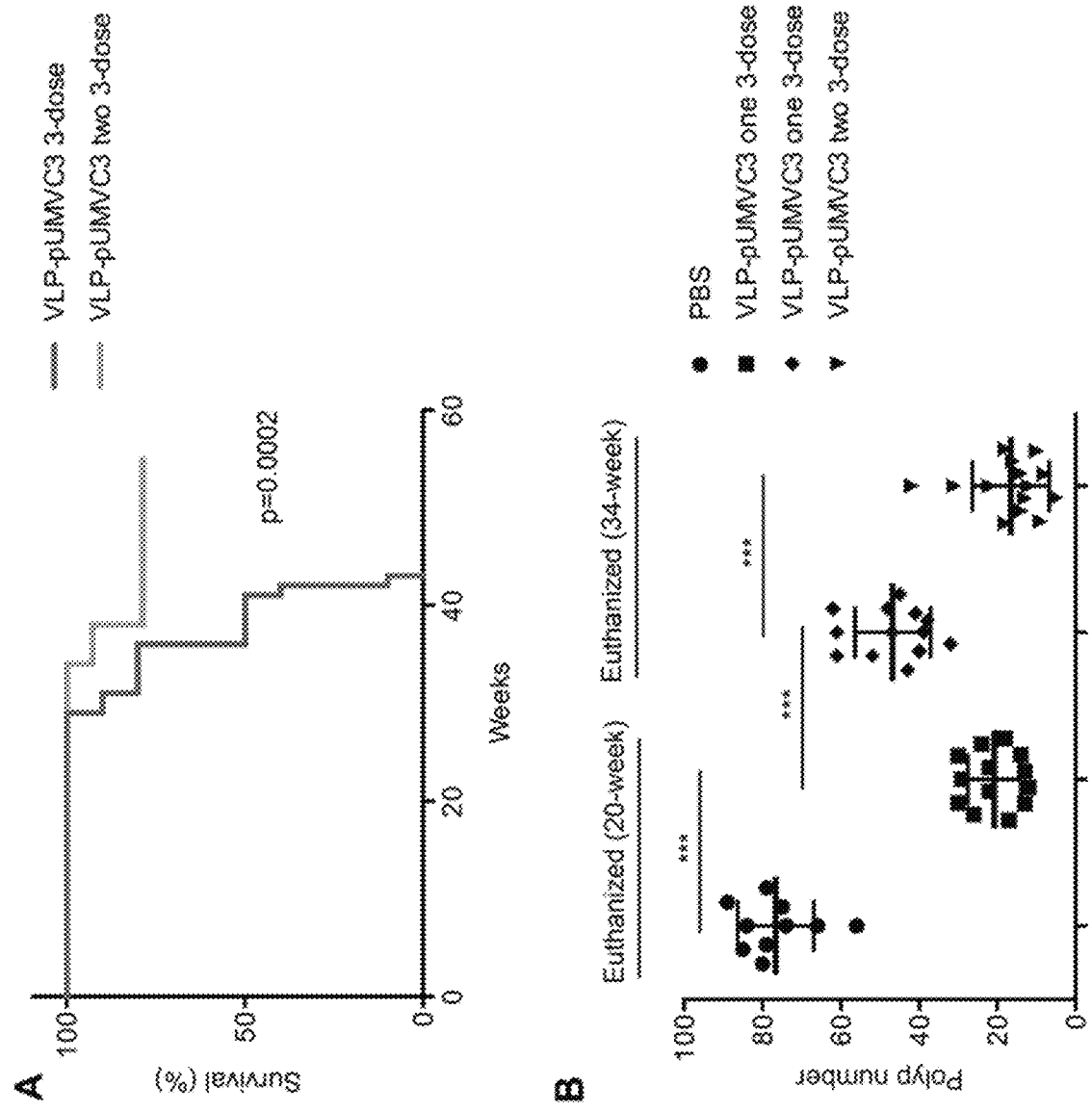
FIG. 14 includes images A and B representing data indicating that PsV immunization frequency positively correlates with the enhanced anti-tumor effect (A) Percentage of survival of Apc$^{Min/+}$ mice that were immunized with one (n=10) or two (n=14) rounds of 3-dose VLP-pUMVC3 vaccination. (B) Numbers of intestinal polyps in Apc$^{Min/+}$ mice that were immunized with one or two rounds of 3-dose VLP-pUMVC3 vaccination. The mice were euthanized either at 20-week or 34-week of age. n=10-13.

The above results indicated that PsV or VLP-induced caspase-1 activation mediates intestinal tumor regression, it was therefore reasoned that increasing immunization frequency might yield an even better tumoricidal efficacy. Indeed, 6 doses of immunizations (8-weeks apart between two consecutive 3-dose immunizations) with VLP-pUMVC3 significantly extended the lifespan of $Apc^{Min/+}$ mice compared with those receiving only three doses of VLP-pUMVC3 immunization (FIG. 14A). The improved lifespan of $Apc^{Min/+}$ mice positively correlates with the enhanced initial tumor eradication efficacy compared to the 3-dose immunization (FIG. 14B).

Figure 5:
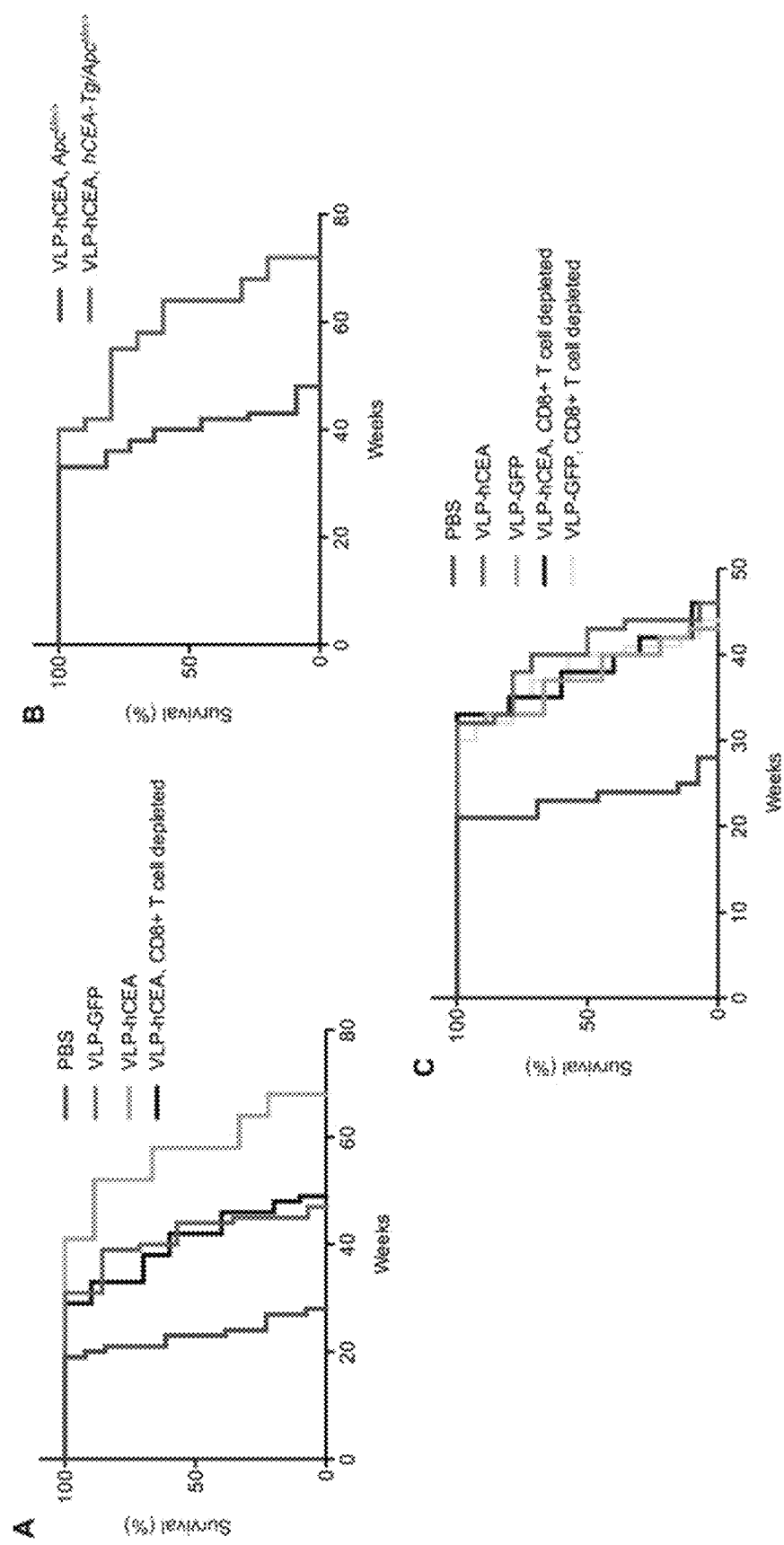
FIG. 5 includes images A through C representing data indicating that PsV-induced tumor antigen-specific CTL response prevents tumor relapse. (A) Survival of hCEA-Tg/Apc$^{Min/+}$ mice that were immunized (one round of 3-dose immunization) with VLP-GFP or VLP-hCEA. One group of mice were pretreated with anti-CD8a antibody to deplete CD8+ T cells before VLP-hCEA immunization. n=9-14 per group. (B) Percentage of survival of Apc$^{Min/+}$ (n=11) or hCEA-Tg/Apc$^{Min/+}$ (n=10) mice that were immunized (one round of 3-dose immunization) with VLP-hCEA. (C) The percentage of survival of Apc$^{Min/+}$ mice that were immunized (one round of 3-dose immunization) with VLP-hCEA or VLP-GFP. Two groups of mice were pretreated with anti-CD8a antibody before VLP-hCEA immunization. n=9-13 per group.

Interestingly, although dispensable for the initial tumor eradication, hCEA-specific immunity delayed tumor relapse after the initial tumor regression in hCEA-Tg/$Apc^{Min/+}$ mice. This was evidenced, at least partially, by the survival advantage of hCEA-Tg/$Apc^{Min/+}$ mice vaccinated with VLP-hCEA, compared to those immunized with VLP-GFP (FIG. 5A). Furthermore, the hCEA-specific protection against intestinal tumor relapse was likely mediated by CTLs because depleting CD8+ T cells prior to and throughout VLP-hCEA immunization approximately reduced the lifespan of hCEA-Tg/$Apc^{Min/+}$ mice to that of VLP-GFP immunized mice (FIG. 5A). Consistent with the finding that hCEA-specific CD8+ T cell response prevented intestinal tumor relapse, it was determined that hCEA expression by intestinal tumor cells was a determinant for preventing tumor relapse because VLP-hCEA immunization led to the enhanced survival of hCEA-Tg/$Apc^{Min/+}$ mice (with hCEA expression in intestinal polyps) relative to that of $Apc^{Min/+}$ mice (no hCEA expression) (FIG. 5B). To further support this concept, VLP-hCEA or VLP-GFP immunized $Apc^{Min/+}$ (lacking hCEA expression) had similar survival time with or without depletion of CD8+ T cells (FIG. 5C). Together, these results indicate that, although dispensable initial tumor eradication, PsV-induced tumor-antigen specific CTL response prevents tumor relapse and extends lifespan of the animal.

The above-described investigations demonstrated that only three doses of PsV immunization can induce remarkable tumor regression and almost triple the animal survival time. Intriguingly, although PsV (i.e. VLP-hCEA) indeed induced humoral and cellular immune responses against the tumor antigen, hCEA, neither CD8+ T cells nor antibodies are required for the PsV-induced tumor regression. Instead, tumor elimination and prolonged animal survival were mainly achieved via activating the innate inflammasome-caspase-1 pathway. Intriguingly, although dispensable for PsV-induced initial tumor eradication, tumor antigen (hCEA)-specific CD8+ T cell response plays a role in preventing tumor relapse, thereby further prolonging the lifespan of the tumor-bearing mice. These investigations expand our current knowledge of cancer immunotherapy that, in addition to adaptive immunity, activation of innate immune pathways can also yield effective anti-tumor activity, thereby providing a basis for future development of a similar approach to combat cancer in patients. Since many types of tumor cells and tumor-associated myeloid cells express inflammasome sensors, it is likely that engaging these innate immune signaling pathways may be beneficial for the treatment of other cancers.

Figure 15:
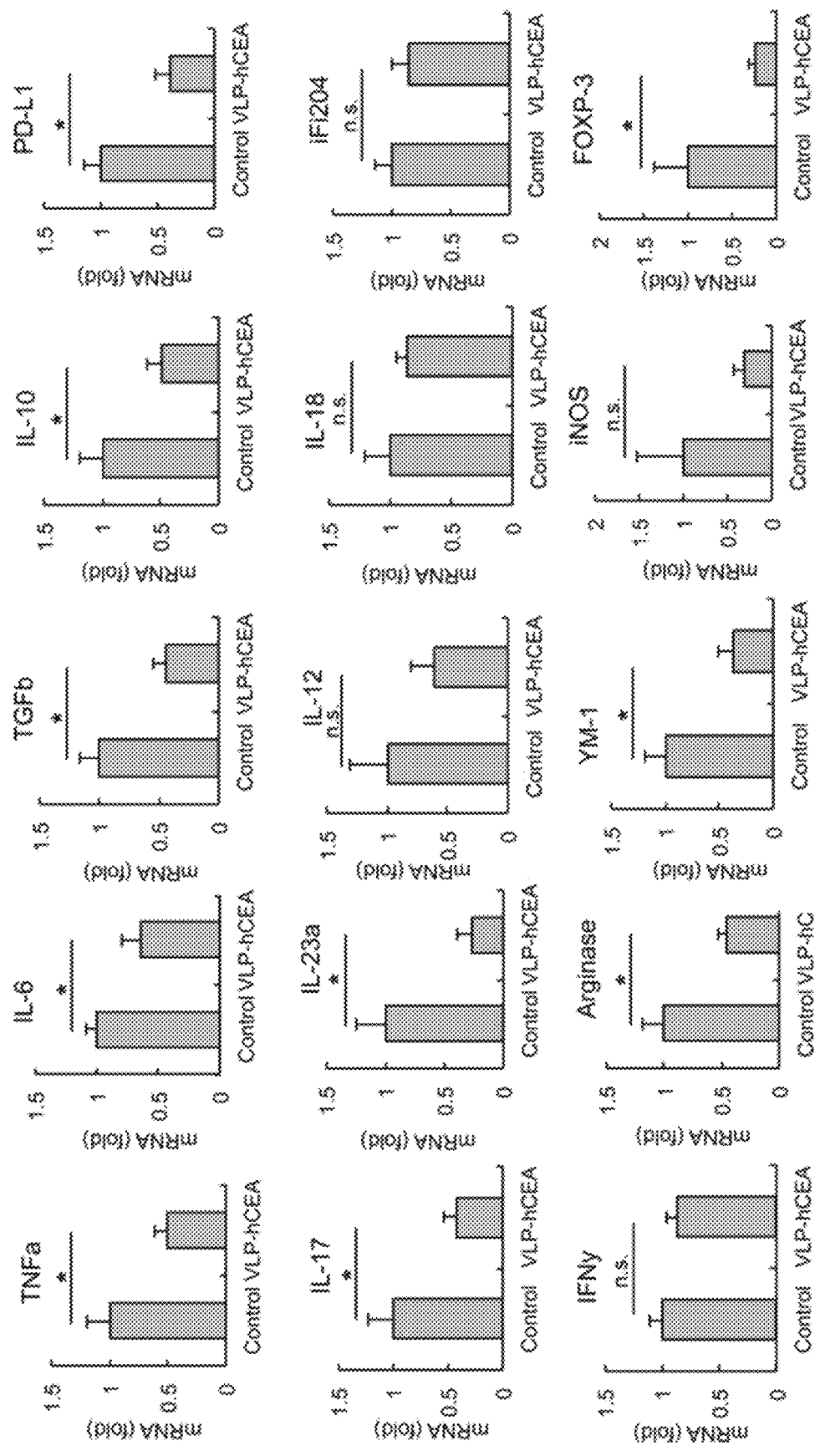
FIG. 15 represents data indicating that VLP-hCEA immunization alters the intestinal tumor microenvironment. 14-week old hCEA-Tg/Apc$^{Min/+}$ mice were orally immunized with VLP-hCEA or PBS. Twenty-four hours post immunization, three small intestinal tumors were collected from individual mice in each group for RNA isolation. The graphs evidence a reduction of tumor-promoting cytokines/M2 markers. Quantitative real-time RT-PCR analysis was performed to determine the expression of indicated genes in tumors. n=3-4. Data are representative of three independent experiments.

The above-noted results suggest that PsV-induced innate immunity exerts anti-tumor effect prior to the induction of adaptive immunity (activation of inflammasome and death of tumor cells can be seen within 48 hours after PsV immunization). Moreover, PsV is known to infect macrophages and dendritic cells. It is theorized that due to the change in intestinal tumor microenvironment after PsV infection, tumor-specific mucosal CTLs induced by PsV immunization might be able to work in a more favorable milieu, thereby preventing tumor relapse and extend the lifespan of tumor-bearing mice. In support of this conclusion, FIG. 15 evidences that a single dose of VLP-hCEA treatment resulted in downregulated expression of a number of immune genes in the tumor tissues that favored tumor growth (i.e. IL-6, TGF-β, IL-10, IL-23A, PD-L1, TNFα, IL-17A, and Foxp3) although not affecting the ones that suppress tumor growth (i.e. IL-12, IFNγ, IL-18, iFi204). FIG. 15 further evidences it was also determined that tumor-promoting cytokines/M2 markers were reduced, in that the expression of M2/tumor associated macrophage (TAM) associated genes (Arginase and Ym-1) was reduced after VLP-hCEA treatment. Inducible nitric oxide synthase (iNOS) that associates with M1 macrophage phenotype was not affected.

Although normal epithelial cells express both NLRP3 and AIM2 innate immune receptors, significant pyroptosis was observed primarily in intestinal tumor cells but not normal epithelial cells. It is theorized that this might be due to a combination of the following reasons. First, it has been shown that PsV and VLP can preferentially infect tumor cells, which could explain the much enhanced pyroptosis in tumor cells versus normal intestinal epithelial cells. Moreover, it was demonstrated that PsV activates the inflammasomes, at least partially, via ROS. It was shown that intestinal tumor cells have high levels of ROS, it was therefore postulated that PsV further enhances production of ROS in the tumor cells, making them more sensitive to inflammasome activation and consequent pyroptosis. Additionally, it is also likely that drastic reduction of mucus deposition surrounding intestinal tumors might make them more accessible to PsV or VLP infection, thereby increasing the load of PsV or VLP which subsequently enhances the magnitude of the PsV- or VLP-induced inflammasome activation and pyroptosis. Moreover, although it is clear that caspase-1 mediated innate immunity and CTL-mediated adaptive immunity are responsible for initial tumor eradication and preventing tumor relapse, respectively, the possibility that PsV or VLP-induced caspase-1 activation might somehow shape the composition of gut microbe community, which might contribute to tumor regression, cannot be completely excluded.

Pre-existing immunity is a concern when a viral vector is used to treat patients as the pre-existing antibodies might neutralize the vector, thereby limiting its efficacy. Although VLP-specific sIgA was not detected in the intestinal washings after the first immunization (data not shown), it clearly did not reduce the efficacy of PsV because two rounds of a three-dose consecutive immunization induced a more remarkable tumor regression and better survival than only one round. This indicates that PsV are not effectively neutralized by sIgA and thus may be used repeatedly, a great advantage for long term therapy. As the tumors are at the apical surface of the intestines, it is possible that the PsV coated with the IgA may still be able to infect tumors, in particular the macrophage population that are associated with tumor cells.

Lastly, immunotherapies with antibodies against CTLA4, PD1 and PDL1/2 have resulted in significant benefit to cancer patients, a rising hope for patients with advanced tumors. By blocking these negative checkpoints, host adaptive immunity may function at the desired efficacy to control tumor growth. However, not all tumors are immunogenic enough to elicit tumor antigen-specific immune responses even when the negative check points are blocked. This may explain ineffectiveness of these antibodies in certain patients, including the ones with colorectal cancer. As the PsV therapeutic strategy disclosed herein targets innate immunity as well as adaptive immunity against tumors, combination of PsV with CTLA-4/PD-1/PD-L1/2 blockade approaches is expected to yield promising success in patients that failed in these checkpoint blockade therapies.

In summary, the above investigations suggest that PsVs, and especially PsVs encoding tumor-specific antigens, may be used as promising anti-tumor therapies, for example, in causing regression of intestinal tumors. Administration of the PsVs to a subject was specifically shown to activate inflammasomes and thereby cause tumor cell pyroptosis and tumor regression. Although PsVs encoding tumor-specific antigens provided the best results, improvements were observed upon administration of blank vector PsVs, as well as PsVs comprising a fluorescent protein. As such, it is within the scope of the invention to produce PsVs for use in anti-tumor therapies, as well as methods of treating patients with such PsVs to induce an inflammatory response in the patients. Such PsVs and treatment methods may be used in the treatment of a variety of adverse conditions.

The above-described investigations were performed using the following materials and methods.

Mice: C57Bl/6 mice, $IIr1^{-/-}$ mice and $Apc^{Min/+}$ mice were purchased from The Jackson Laboratory (Bar Harbor, Me.). hCEA-Tg [CEA.Tg, Line 2682, C57Bl/6 (H-2b), heterozygous] mice were originally obtained from Dr. John Thompson (University of Freiburg, Freiburg, Germany) and kindly provided by Drs. John W. Greiner and Jeffrey Schlom (National Cancer Institute, NIH, Bethesda, Md.). The hCEA-Tg mouse colony is maintained with continuous backcrossing with C57Bl/6 mice since the year of 1999. Transgenic mice were generated from C57Bl16×CB6 F1 mice (Ciba Animal Breeding Center, Basel, Switzerland) and lines were established from founder animals by mating with C57Bl16 mice. The hCEA-Tg and $Apc^{Min/+}$ mouse colonies were maintained by continuous backcrossing with C57Bl/6 mice since 1999. hCEA-Tg/$Apc^{Min/+}$ mice were generated by crossing male $Apc^{Min/+}$ mice with female hCEA-Tg mice. hCEA-Tg/$Apc^{Min/+}$/$IL\text{-}1r1^{-/-}$ mice were generated by crossing the hCEA-Tg/$Apc^{Min/+}$ mice with $IIr1^{-/-}$ mice. All mice were maintained under specific pathogen-free conditions. All experimental procedures were carried out according to the protocols approved by the Institutional Animal Care and Use Committee.

Cells and Reagents: ATP, PMA, cytochalasin D and BAPTA-AM were from Sigma-Aldrich. Ultrapure LPS was from Invivogen. DPI was from Calbiochem. Lipofectamine 2000 and MitoSOX were from Life Technologies. Calcium-free and calcium-containing DMEM media were from US Biologicals. Caspase-1 inhibitor Z-YVAD-FMK (SEQ ID NO: 37) and caspase-3 inhibitor Z-DEVD-FMK (SEQ ID NO: 38) were from Enzo Life Sciences. The lactate dehydrogenase (LDH) assay kit and in situ cell death detection kit (TUNEL) were from Roche. FLICA capase-1 kit was from Immunochemistry. Antibodies used for immunoblotting were as follows: anti-mouse caspase-1 (AG-20B-0042-C100, Adipogen), anti-mouse β-actin (sc-1615 HRP, Santa Cruz Biotechnology) and anti-mouse IL-1β (AF-401-NA, R&D Systems). Imject Alum and streptavidin-HRP were from Pierce.

Generation of papillomavirus virus-like particles and pseudoviruses: The C-terminal truncated bovine papillomavirus-1 (BPV-1) L1 capsid protein were used to generated VLP using the recombinant baculovirus expression system and purified as described. The hCEA expression plasmid pUMVC3-hCEA encoding human carcinoembryonic antigen without the NH2-terminal signal peptide was constructed by ligation of EcoRI and NotI enzyme digested hCEA gene fragment from pCI-CEA plasmid6 with pUMVC3 vector plasmid. The CEA gene sequence and protein expression were verified by sequencing and immunoblot analysis. BPV L1 pseudoviruses were generated as described. Briefly, purified VLP were dialyzed against 10 mmol/L HEPES solution, and then VLP (40 µg) were disrupted at the condition of 25 mmol/L Tris-HCl (pH 8.0), 15 mmol/L NaCl, 10 mmol/L EGTA, and 20 mmol/L DTT in a final volume of 200 µL at room temperature for 60 minutes. Then, 1 µg/µL plasmid pUMVC3-hCEA, pUMVC3-GFP (expression green fluorescent protein) or pUMVC3 vector (20 µL) was added and the mixture was diluted by 220 µL reassembly buffer containing 25 mmol/L CaCl2 and 20% DMSO to form pseudoviruses at room temperature for 4 hours. The reassembled pseudovirus particles were verified by Zeiss EM900 electron microscopy as described previously. The efficiency of plasmid DNA encapsidation in the VLP was analyzed by measuring the amount of DNA plasmid inside of the VLP as described previously. Briefly, VLP-hCEA or VLP-pUMVC3 pseudovirus preparation (100 µL) was treated with 80 units Benzonase (Sigma) for 1 hour at 37° C. and heated at 100° C. for 10 minutes, and then digested with proteinase K (1 mg/mL) at 55° C. for 3 hours. The remaining plasmid DNA was extracted and the amount of plasmid DNA was determined by UV spectrophotometry quantitation. The amount of the plasmid DNA packaged inside of VLP was used to determine the copy numbers of the pseudovirus.

Cell culture and stimulation: Bone marrow derived macrophages (BMDM) were generated by culturing the mouse bone marrow cells in the presence of 20% vol/vol L929 conditional media as previously described. Immortalized murine macrophages from $Nlrp3^{-/-}$, $Capase\text{-}1^{-/-}$, $Nlrc4^{-/-}$, $Cathepsin\ B^{-/-}$ mice and their corresponding wild-type control cells were generously provided by Dr. Katherine Fitzgerald and as previously described. After pretreatment with ultrapure LPS (100 ng/ml) for primary or immortalized BMDM, the cells were then stimulated with ATP for 30 min and VLP or pseudovirus for 18 h. Plasmid were transfected into macrophages using Lipofectamine 2000 according to manufacturer's instructions. In the experiments using chemical inhibitors, they were added 1 h before inflammasome agonists. After inflammasome agonists stimulation, culture supernatants and cell lysates were collected for ELISA and immunoblot analysis.

Vaccination and sample collection: 14-week old $Apc^{Min/+}$, hCEA-Tg/$Apc^{Min/+}$ or hCEA-Tg/$Apc^{Min/+}$/$IL\text{-}1r1^{-/-}$ mice were used for the therapeutic vaccination experiments. For oral immunization, mice were immunized three times at a 2-week interval by oral gavage with either Phosphate Buffered Saline (PBS), 20 µg BPV VLP or $0.8\sim1\times10^{11}$ VLP-hCEA, VLP-pUMVC3 or VLP-GFP pseudovirions generated from 20 µg BPV VLP. In another set of immunization, mice were orally immunized three times as described above and were received another round of three-time immunization 8 weeks after the first round of immunization. Two weeks after the third immunization or after the second round of three-time immunization, mice were sacrificed and serum, intestinal washing and whole small intestines were collected from individual mouse for the subsequent experiments. Fecal samples were collected individually before mice sacrifice. For caspase inhibitor treatment, mice were received caspase-1 inhibitor Z-YVAD-FMK (SEQ ID NO: 37) (5 mg/kg of body weight in 150 µl volume), caspase-3 inhibitor Z-DEVD-FMK (SEQ ID NO: 38) or the corresponding diluent (3% dimethyl sulfoxide, in phosphate-buffered saline) by intraperitoneal (i.p.) injection on days -1, 0, 1 of each immunization and every 3 days during the interval of immunization. The mice were under treatment till two weeks after final immunization.

Spleen to body weight ratio, body weight and survival: After euthanasia, mice body weight was measured, and then mice spleens were collected and spleen weight was measured. The ratios of spleen to body weight were calculated as spleen weight/body weight. Mice body weights were measured 2 weeks after the third immunization (20-week old). Mice survival (whether found dead or euthanized) was monitored every other day after immunization. When they became moribund, they were considered to have reached the experimental endpoint and were then euthanized.

Isolation of lymphocytes from spleen and Peyer's patches: Lymphocytes from spleen and Peyer's patches were isolated as described. Briefly, mouse spleen was homogenized and followed by treatment with ACK lysis buffer to lyses red blood cells. The single-cell suspension was collected by passing splenocytes through 70 µm cell strainers (BD Biosciences, Bedford, Mass.). Then, the cell suspension was incubated in nylon-wool columns (Polysciences, Warrington, Pa.) at 37° C. for 1 hour and the enriched T cells were washed through the columns with complete RPMI 1640. To isolate lymphocytes from Peyer's patches, visible Peyer's patches were harvested from ice-cold PBS flushed small intestines. After homogenization, cells were passed through 70 µm cell strainers and lymphocytes were isolated by Ficoll gradient separation (GE Healthcare). Population of T cells were analyzed by flow cytometry (data not shown) and no significant difference was found in cell composition for splenocytes and Peyer's patch lymphocytes from different treatment groups.

Tumor staining and quantification: Methylene blue dye was used for staining of intestinal tumors. Briefly, mouse small intestines were collected from each group and flushed with cold PBS to remove the fecal contents. Intestines were then opened and rinsed in 1% methylene blue dye for 1 hour at room temperature. The excessive methylene blue dye was washed out by rinsing the intestines with PBS overnight. The tumor numbers and sizes were assessed by measuring the deep stains in intestine. The staining results were recorded with photographs. The small intestine was divided into three equal parts and tumor numbers were counted and grouped based on sizes: <1 mm, 1-3 mm and >3 mm.

In vivo depletion of CD8+ T cells and serum transfer: For CD8$^+$ T cell depletion, mice were intraperitoneally (i.p.) injected with 250 µg of anti-CD8a IgG2a antibody (from Cedarlane) at 2- and 1-day before every pseudovirus immunization. During the interval of immunization, mice were given additional 250 µg of anti-CD8a antibody every 3 days until the end of the experiment. Control mice were i.p. injected with 250 µg of IgG2a isotype control antibody with the same schedule. Efficiency of CD8$^+$ T cell depletion in spleen and Peyer's patch was verified 1 day after two rounds of depleting-antibody injection. For serum transfer, sera collected from VLP-hCEA treated or control mice were pooled respectively and transferred to 14-week old hCEA-Tg/Apc$^{Min/+}$ mice i.p. (200 µl/dose) for 3 times at two-week intervals. Two weeks after the third transfer, mice were euthanized and intestines were isolated and subjected to intestinal tumor staining as described above.

Isolation of phagocytes from small intestine: Isolation of small intestinal mononuclear phagocytes was performed as previously described with modifications. Briefly, small intestine isolated from individual mouse was inverted on a polyethylene tube (BD Biosciences), and washed with Calcium and Magnesium free PBS. Then, the mucus was removed by treating with 1 mM dithiothreitol (Sigma). After wash, the intestine was incubated twice with 30 mM EDTA for 10 min to elute epithelium, followed by incubation with 36 U/ml collagenase IV (Sigma) and 500 U/mL of DNase I (Thermo Scientific) in PBS for 90 min at 37° C. The digested tissue was then passed through a 70-µm Cell Strainer (BD Biosciences) and washed with DMEM. Mononuclear phagocytes were collected from an OptiPrep (Sigma) density centrifugation. Macrophages were enriched by incubating single cell suspension obtained above with CD11 b MACS beads according to manufacturer's instructions (Miltenyi Biotec). Bead-attached cells were separated by positive selection using MACS LS magnetic column and cultured in RPMI1640 with 100 U/mL penicillin, 100 µg/mL streptomycin, and 10% FBS.

CTL assay: The cytotoxicity was measured by a standard 6-hour $^{51}$Cr release assay as described. Briefly, Peyer's patch lymphocytes were pooled from three to four mice per group and were directly used as effector cells for the mucosal CTL assay. Enriched T cells from individual mouse spleen were in vitro stimulated for 5 days and then used as effector cells for the systemic CTL assay. Enriched splenic-T cells were cultured in RPMI 1640 with 5 µg/mL hCEA peptide (CEA526-533 EAQNTTYL (SEQ ID NO: 35)) and 5% T-stim without concanavalin A (BD Discovery Labware). Irradiated splenocytes from WT C57BL/6 mice were used as feeder cells for in vitro stimulation. RMA cells were used as target cells by incubating at 37° C. with 200 µCi sodium chromate (Perkin-Elmer, Boston, Mass.) for 1 hour. Effector cells from Peyer's patches or spleen were seeded into triplicate wells containing the target cells at various effector/target (E:T) cell ratios in the presence of hCEA peptide or control peptide (LCMV Gp33 KAVYNFATC (SEQ ID NO: 36)). Plates were incubated at 37° C. with 5% (v/v) $CO_2$ for 6 hours. Then, the supernatant was removed from each well and the $^{51}$Cr release was assessed using a gamma radiation counter (Perkin-Elmer). The calculation of specific cell lysis (%) was described.

Enzyme-linked immunosorbent assay: Sera, intestinal washings or fecal extractions from Apc$^{Min/+}$ or hCEA-Tg/Apc$^{Min/+}$ mice that were orally immunized with PsV or VLP were used for detecting anti-hCEA antibody response or the presence of mouse albumin by ELISA. For anti-hCEA antibody detection, the plates were coated with 100 µL/well hCEA (Fitzgerald, Concord, Mass.) at a concentration of 2 µg/mL overnight. For albumin detection, plates were coated with 1 µg/mL of anti-albumin capture antibody overnight. Then, wells were blocked with 5% nonfat dry milk in PBS-T for one hour. The plates were then incubated with serially diluted mouse sera, intestinal washings or fecal extractions for one hour followed by one-hour incubation with horseradish peroxidase (HRP)-conjugated anti-mouse IgG (Pierce), HRP-conjugated anti-mouse IgA (Sigma-Aldrich)

or HRP-conjugated anti-mouse albumin antibody (Bethyl laboratories, Inc). 3,3' 5,5'-tetramethylbenzidine (Sigma) were used as substrate. The reaction was stopped by 1 M $H_2SO_4$ and the optical density (OD) of each well was measured at a wavelength of 450 nm. For the measurement of mouse IL-1β, paired (capture and detection) antibodies and standard recombinant proteins were purchased from eBioscience. Mouse IL-18 was quantified using commercially available ELISA kit (eBioscience) according to the manufacturer's instructions.

Real-time PCR: Intestinal tissues (non-tumor or tumor) were collected from individual mouse in each group for RNA isolation. RNA was isolated and reverse transcribed using Reverse Transcription Supermix (BioRad Laboratories, Inc). Quantitative real-time PCR analysis was performed in 96-well PCR plates using the CFX96 Touch Real-Time PCR Detection System (BioRad Laboratories, Inc). All gene expression data are presented as the expression relative to GAPDH. The primer sequence for the target genes are obtained from primerbank (http://pga.mgh.harvard.edu/primerbank/) and described in the following Table 1.

TABLE 1

Primers sequences for real-time PCR analysis (SEQ ID NOS 1-34, respectively, in order of appearance).

| Mouse gene | Forward | Reverse |
|---|---|---|
| TNFα | AGGGTCTGGGCCATAGAACT | CCACCACGCTCTTCTGTCTAC |
| TGFβ1 | CAACCCAGGTCCTTCCTAAA | GGAGAGCCCTGGATACCAAC |
| Foxp3 | CTCGTCTGAAGGCAGAGTCA | TGGCAGAGAGGTATTGAGGG |
| IFN-γ | GAGCTCATTGAATGCTTGGC | GCGTCATTGAATCACACCTG |
| iNOS | GTTCTCAGCCCAACAATACAAGA | GTGGACGGGTCGATGTCAC |
| Arginase | TGGCTTGCGAGACGTAGAC | GCTCAGGTGAATCGGCCTTTT |
| YM1 | TTATCCTGAGTGACCCTTCTAAG | TCATTACCCTGATAGGCATAGG |
| IL-1β | AGGTCAAAGGTTTGGAAGCA | TGAAGCAGCTATGGCAACTG |
| IL-18 | TCCTTGAAGTTGACGCAAGA | TCCAGCATCAGGACAAAGAA |
| IL-6 | ACCAGAGGAAATTTTCAATAGGC | TGATGCACTTGCAGAAACA |
| IL-10 | TGTCAAATTCATTCATGGCCT | ATCGATTTCTCCCCTGTGAA |
| IL-12 | GCTTCTCCCACAGGAGGTTT | CTAGACAAGGGCATGCTGGT |
| IL-17A | TGAGCTTCCCAGATCACAGA | TCCAGAAGGCCCTCAGACTA |
| IL-23a | GCTCCCCTTTGAAGATGTCA | GACCCACAAGGACTCAAGGA |
| PDL-1 | GCTCCAAAGGACTTGTACGTG | TGATCTGAAGGGCAGCATTTC |

TABLE 1-continued

Primers sequences for real-time PCR analysis (SEQ ID NOS 1-34, respectively, in order of appearance).

| Mouse gene | Forward | Reverse |
|---|---|---|
| iFi204 | TCTTTTCTGGGCTGTGGAAG | ACAGCTCAGGCGAGGACTT |
| GapDH | TTGATGGCAACAATCTCCAC | CGTCCCGTAGACAAAATGGT | siRNA knocking down: siRNAs specific for mouse Aim2 or Ifi204 were purchased from Santa Cruz Biotechnology, and were used under manufacturer's instructions.

Mitochondrial ROS detection: The measurement of mitochondrial ROS was as previously described. Briefly, WT BMDMs from C57Bl/6 mice were treated with VLP for 6 h, and then loaded with 4 µM of MitoSOX (Life Technologies) for 15 min. After that, the cells were washed three times with sterile PBS and subjected to flow cytometric analysis. Mean fluorescence intensity was determined using a FACS Canto-flow cytometer (BD Bioscience), and data were analyzed using FlowJo software (Treestar).

Detection of active caspase-1 in vivo: 14-week old $Apc^{Min/+}$ mice were immunized with VLP-hCEA via oral gavage. 48 hours later, intestinal tumor polyps from small intestine were collected and snap frozen. Frozen sections were then subjected for co-staining with DAPI, FAM-FLICA caspase-1 probe and A594-conjugated anti-mouse F4/80 (Biolegend) or DAPI, FAM-FLICA caspase-1 probe and anti-mouse EpCAM (Abcam) antibody. A594-conjugated anti-Rat IgG was used as the secondary antibody.

Detection of PsV infection in vivo: VLP-GFP pseudovirus ($1 \times 10^{11}$ virus particles) was given to 14-week old $Apc^{Min/+}$ mice via oral gavage. 24 hours after, tumor polyps from small intestine were isolated and snap frozen. Sections of tissue were subjected for co-staining with DAPI, anti-GFP (Thermo scientific) and A594-conjugated anti-mouse F4/80 (Biolegend) or DAPI, anti-GFP and anti-mouse EpCAM (Abcam) antibody.

TUNEL staining: 14-week old hCEA-Tg/$Apc^{Min/+}$ mice were orally immunized with VLP-hCEA. 48 hours post immunization, tumor polypus from small intestine were isolated and snap frozen. TUNEL staining was performed in frozen tissue sections to determine the cell death in vivo. Co-staining of mouse F4/80 (Biolegend) or mouse EpCAM (Abcam) were performed after TUNEL staining.

Analysis of caspse-1 activation by Western blot: 14-week old $Apc^{Min/+}$ mice were immunized with VLP-hCEA orally. 24 and 48 hours later, intestinal tumor polyps were collected and lysed for cellular protein extraction. Protein extractions were then subjected to SDS-PAGE, electro-blotted to a nitrocellulose membrane and immunoblotted against mouse caspase-1 p20 fragment (AdipoGen) or anti β-actin (Biolegend).

Analyzing the efficacy of IL-18 neutralization in vivo: Firstly, to analyze the efficacy of L-18 neutralization in vivo, anti-mouse IL-18 neutralizing antibody (R&D system) or a control antibody (rat IgG1) was given to $Apc^{Min/+}$ mice by i.p. (200 µg/dose) on days −1, 1 of VLP-hCEA oral immunization. Mice were sacrificed at day 2. In control group, after anti-IL-18 antibody or control IgG1 treatment as described above, LPS (Invivogen) were given to mice i.p. (200 µg/mouse) at day 2 and mice were sacrificed 6 hours after injection. Blood and whole small intestines were collected for serum isolation and intestinal homogenization, respectively. Intestines were washed with cold PBS twice and extra liquid were removed by brief spinning. Each small intestine was divided into 2 parts: upper half and lower half. Intestines were washed with cold PBS twice and extra liquid were removed by brief spinning. Then, intestinal tissues were weighted and homogenized in PBS with 2× proteinase inhibitor cocktail followed by centrifuge at 5000 rpm for 10 min. Supernatant were collected and the volume of each sample was measured. IL-18 concentrations in tissue homogenization were measured by ELISA and calculated as pg/mg tissue. Data are representative of two independent experiments. Data shown as mean±SD. n=3 in each group. To test the effect of IL-18 in PsV- or VLP-induced tumoridical effect, anti-mouse IL-18 antibody or rat IgG1 isotype control antibody was given to hCEA-Tg/Apc$^{Min/+}$ mice i.p. (200 μg/dose) on days −1, 1 of each immunization and every 3 days during the interval of immunization. The mice were under treatment until two weeks after final immunization.

Statistical analysis: All data are shown as mean±s.d. or mean±s.e.m. For comparison of two groups, significance was analyzed by Student's t-test, whereas Kruskal-Wallis test was used to compare three or more groups. Log-rank test was used will be used for survival analysis. For all tests, P-values <0.05 were considered statistically significant.

While the invention has been described in terms of specific or particular embodiments and investigations, it is apparent that other forms could be adopted by one skilled in the art. For example, on the basis of the research described above, it was concluded that inflammasome activators other than papilloma pseudoviruses and papilloma virus-like particles could be used to treat tumors other than gastrointestinal tumors. Furthermore, it is believed such inflammasome activators may comprise an anti-tumor antigen other than those disclosed herein, inflammasomes may be activated by another means, processing parameters such as temperatures and durations could be modified, and other methods of producing the papilloma pseudovirus and papilloma virus-like particles could be used. Accordingly, it should be understood that the invention is not limited to any embodiment described herein. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A method of treating a tumor in a subject, the method comprising:
   administering a composition to the subject, wherein the composition includes an inflammasomes activator comprising a papilloma pseudovirus or a papilloma virus-like particle, wherein the papilloma pseudovirus or the papilloma virus-like particle activates inflammasomes in cells of the tumor and thereby causes tumor cell pyroptosis and tumor regression in the tumor; wherein the papilloma pseudovirus or the papilloma virus-like particle does not encode a tumor-associated antigen; and
   wherein the papilloma pseudovirus or the papilloma virus-like particle includes a blank (empty) vector.

2. The method of claim 1, wherein the tumor is a gastro-intestinal tumor.

3. The method of claim 1, wherein the composition is delivered to gastro-intestinal mucosal tumors.

4. The method of claim 1, wherein the papilloma pseudovirus or the papilloma virus-like particle includes a protein.

5. The method of claim 1, wherein the papilloma pseudovirus or the papilloma virus-like particle includes a fluorescent protein.

6. The method of claim 1, wherein the papilloma pseudovirus or the papilloma virus-like particle induces pyroptosis of macrophages in the tumor.

7. The method of claim 1, wherein the papilloma pseudovirus or the papilloma virus-like particle induces a reduction of tumor-promoting cytokines/M2 markers in the tumor.

8. The method of claim 1, wherein the papilloma pseudovirus or the papilloma virus-like particle kills myeloid cells.

9. A method of treating a tumor in a subject, the method comprising:
   administering a composition to the subject, wherein the composition includes a papilloma pseudovirus or a papilloma virus-like particle that includes a blank (empty) vector and activates inflammasomes in cells of the tumor and thereby causes tumor cell pyroptosis and tumor regression in the tumor.

10. The method of claim 9, wherein the tumor is a gastro-intestinal tumor.

11. The method of claim 9, wherein the composition is delivered to gastro-intestinal mucosal tumors.

12. The method of claim 9, wherein the papilloma pseudovirus or papilloma virus-like particle induces pyroptosis of macrophages in the tumor.

13. The method of claim 9, wherein the papilloma pseudovirus or papilloma virus-like particle induces a reduction of tumor-promoting cytokines/M2 markers in the tumor.

\* \* \* \* \*

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      TNF-alpha forward primer

<400> SEQUENCE: 1
agggtctggg ccatagaact                                                      20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      TNF-alpha reverse primer

<400> SEQUENCE: 2
ccaccacgct cttctgtcta c                                                    21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      TNF-beta1 forward primer

<400> SEQUENCE: 3
caacccaggt ccttcctaaa                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
```

TNF-beta1 reverse primer

<400> SEQUENCE: 4
ggagagccct ggataccaac                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Foxp3 forward primer

<400> SEQUENCE: 5
ctcgtctgaa ggcagagtca                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Foxp3 reverse primer

<400> SEQUENCE: 6
tggcagagag gtattgaggg                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      INF-gamma forward primer

<400> SEQUENCE: 7
gagctcattg aatgcttggc                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      INF-gamma reverse primer

<400> SEQUENCE: 8
gcgtcattga atcacacctg                                                   20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      iNOS forward primer

<400> SEQUENCE: 9
gttctcagcc caacaataca aga                                               23

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      iNOS reverse primer

<400> SEQUENCE: 10
gtggacgggt cgatgtcac                                                    19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Arginase forward primer

<400> SEQUENCE: 11
tggcttgcga gacgtagac                                                    19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      Arginase reverse primer

<400> SEQUENCE: 12
gctcaggtga atcggccttt t                                                 21

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      YM1 forward primer

<400> SEQUENCE: 13
ttatcctgag tgaccctttct aag                                              23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      YM1 reverse primer

<400> SEQUENCE: 14
tcattaccct gataggcata gg                                                22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-1-Beta forward primer

<400> SEQUENCE: 15
aggtcaaagg tttggaagca                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-1-Beta reverse primer

```
<400> SEQUENCE: 16
tgaagcagct atggcaactg                                        20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-18 forward primer

<400> SEQUENCE: 17
tccttgaagt tgacgcaaga                                        20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-18 reverse primer

<400> SEQUENCE: 18
tccagcatca ggacaaagaa                                        20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      IL-6 forward primer

<400> SEQUENCE: 19
accagaggaa attttcaata ggc                                    23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-6 reverse primer

<400> SEQUENCE: 20
tgatgcactt gcagaaaaca                                        20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      IL-10 forward primer

<400> SEQUENCE: 21
tgtcaaattc attcatggcc t                                      21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-10 reverse primer

<400> SEQUENCE: 22
```
atcgatttct cccctgtgaa                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-12 forward primer

<400> SEQUENCE: 23
gcttctccca caggaggttt                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-12 reverse primer

<400> SEQUENCE: 24
ctagacaagg gcatgctggt                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-17A forward primer

<400> SEQUENCE: 25
tgagcttccc agatcacaga                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-17A reverse primer

<400> SEQUENCE: 26
tccagaaggc cctcagacta                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-23a forward primer

<400> SEQUENCE: 27
gctccccttt gaagatgtca                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      IL-23a reverse primer

<400> SEQUENCE: 28
gacccacaag gactcaagga                                        20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      PDL-1 forward primer

<400> SEQUENCE: 29
gctccaaagg acttgtacgt g                                      21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      PDL-1 reverse primer

<400> SEQUENCE: 30
tgatctgaag ggcagcattt c                                      21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      iFi204 forward primer

<400> SEQUENCE: 31
tcttttctgg gctgtggaag                                        20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      iFi204 reverse primer

<400> SEQUENCE: 32
acagctcagg cgaggactt                                         19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      GapDH forward primer

<400> SEQUENCE: 33
ttgatggcaa caatctccac                                        20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      GapDH reverse primer

<400> SEQUENCE: 34
cgtcccgtag acaaaatggt                                        20

```
<210> SEQ ID NO 35
<211> LENGTH: 8
<212> TYPE: PRT
<213> ORGANISM: Homo sapiens

<400> SEQUENCE: 35

Glu Ala Gln Asn Thr Thr Tyr Leu
1               5

<210> SEQ ID NO 36
<211> LENGTH: 9
<212> TYPE: PRT
<213> ORGANISM: Lymphocytic choriomeningitis virus

<400> SEQUENCE: 36

Lys Ala Val Tyr Asn Phe Ala Thr Cys
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Val Ala Asp
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Glu Val Asp
1
```